(12) United States Patent
Fuchs et al.

(10) Patent No.: US 7,196,191 B2
(45) Date of Patent: Mar. 27, 2007

(54) CATALYTIC OXIDATION OF C—H BONDS

(75) Inventors: Philip Fuchs, West Lafayette, IN (US); Seongmin Lee, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 341 days.

(21) Appl. No.: 10/636,129

(22) Filed: Aug. 7, 2003

(65) Prior Publication Data

US 2004/0087820 A1    May 6, 2004

Related U.S. Application Data

(60) Provisional application No. 60/403,498, filed on Aug. 14, 2002.

(51) Int. Cl.
*C07J 71/00* (2006.01)
*C07J 21/00* (2006.01)
*C07J 33/00* (2006.01)
*C07J 43/00* (2006.01)

(52) U.S. Cl. .......................... 540/19; 549/344
(58) Field of Classification Search ................. 540/19; 549/344
See application file for complete search history.

(56) References Cited

OTHER PUBLICATIONS

Lee et al., J. Am. Chem. Soc. 2002, 124, 13978-13979.*
Yamazaki, Tetrahedron Letters 42 (2001) 3355-3357.*
LaCour et al., J. Am. Chem. Soc. 1998, 120, 692-707.*
Hentenmann et al., Tetrahedron Lett. 40,2699-2702 (1999).
Evarts et al., Tetrahedron Lett., 40, 2703-2706 (1999).
Hentenmann et al., Organic Lett., 1, 355-357 (1999).
Jiang et al., Organic Lett., 2, 2181-2184 (2000).
Tong, et al., Tetrahedron Lett. 41, 7795-7799 (2000).
Evarts et al., Tetrahedron Lett., 3673-3675 (2001).
Myers et al., J. Org. Chem., 67, 200-204 (2002).
Torres et al., Angew. Chem. Int. Ed., 42, 3124-3131 (2003).
Guo, C. et al. "An Efficient Protocol for the Synthesis of Unsymmetrical Pyrazines. Total Synthesis of Dihydrocephalostatin 1" J. Am. Chem. Soc. 1996, 118:10672-10673.
Jeong, J.U. et al. Biomimetic Total Synthesis of (+)-Cephalostatin 7, (+) -.
Cephalostatin 12, and (+)-Ritterazine K J. Am. Chem. Soc. 1995, 117:10157-10158.
Li, W. et al. "An Efficient Synthesis of the C-23 Deoxy, 17alpha-Hydroxy South 1 Hemisphere and Its Cephalostatin 1 Analog" Org. Lett. 2003, 5:2849-2852.
Liu, Z. et al. "Intermolecular C—N Addition of Amides and S—N Addition of Sulfinamides to Arynes" J. Am. Chem. Soc. 2005, 127:13112-13113.
Jeong, J.U. et al. "Synthesis of the South Unit of Cephalostatin. 7. Total Synthesis of (+)-Cephalostatin 7, (+)-Cephalostatin 12, and (+)-Ritterazine K" J. Am. Chem. Soc 1999, 121:2071-2084.
Kim, S. et al. "Synthesis of the North 1 Unit of the Cephalostatin Family from Hecogenin Acetate" J. Am. Chem. Soc. 1999, 121:2056-2070.
LaCour, T.G. et al. "Interphylal Product Splicing: The First Total Syntheses of Cephalostatin 1, the North Hemisphere of Ritterazine G, and the Highly Active Hybrid Analogue, Ritterostatin $G_N1_N$" J. Am. Chem. Soc. 1999, 120:692-707.
Evarts, J. et al. "Syntheses of Highly Substituted Enantiopure C6 and C7 Enones" J. Am. Chem. Soc. 2002, 124:11093-11101.

* cited by examiner

*Primary Examiner*—Joseph K. McKane
*Assistant Examiner*—Rebecca Anderson
(74) *Attorney, Agent, or Firm*—Henry D. Coleman; R. Neil Sudol; William J. Sapone

(57) ABSTRACT

The invention provides a catalytic, chemospecific and stereospecific method of oxidizing a wide variety of substrates without unwanted side reactions. Essentially, the method of the instant invention, under relatively mild reaction conditions, catalytically, stereospecifically and chemospecifically inserts oxygen into a hydrocarbon C—H bond. Oxidation (oxygen insertion) at a tertiary C—H bond to form an alcohol (and in some cases a hemiacetal) at the tertiary carbon is favored. The stereochemistry of an oxidized tertiary carbon is preserved. Ketones are formed by oxidizing a secondary C—H bond and ring-cleaved diones are formed by oxidizing cis tertiary CH bonds.

11 Claims, 18 Drawing Sheets

Scheme 1

C_{29}H_{41}IO_5
Mol. Wt.: 596.54

CATALYTIC OXIDATION OF C—H BONDS

RELATED APPLICATIONS

This application claims the benefit of priority from provisional application No. 60/403,498, filed Aug. 14, 2002.

The present invention was made with support from a grant of the National Institutes of Health, grant no. CA60548. Consequently, the government retains certain rights in the invention.

FIELD OF THE INVENTION

The invention provides a catalytic, chemoselective (preferably, chemospecific) and stereoselective (preferably, stereospecific) method of oxidizing a wide variety of substrates without unwanted side reactions. Essentially, the method of the instant invention, under relatively mild reaction conditions, catalytically, stereospecifically and chemospecifically inserts oxygen into a hydrocarbon C—H bond. Oxidation (oxygen insertion) at a tertiary C—H bond to form an alcohol (and in some cases a hemiacetal) is favored. Ketones are formed by oxidizing a secondary C—H bond, while diones are formed from cleavage of 1,2 diols formed from oxidation of adjacent tertiary C—H's which are cis. The stereochemistry of an oxidized tertiary carbon is preserved.

BACKGROUND OF THE INVENTION

As disclosed in U.S. Pat. No. 6,384,251, organic compounds having an allylic hydrogen atom(s) have been reacted with a combination of a chromium compound and an N-hydroxy dicarboxylic acid imide under conditions sufficient to affect oxidation of the allylic hydrogen(s) on the organic compound. Similarly, U.S. Pat. No. 6,111,118 discloses that olefinic compounds can be allylically oxidized by: (i) dissolving the olefinic compound in a suitable mixture of a water miscible organic solvent, a water immiscible organic solvent and the alkyl hydroperoxide, (ii) incorporating periodic acid or metal periodate and a suitable amount of water into the reaction mixture, and then (iii) optionally pressurizing the reaction vessel with air or nitrogen.

Reaction with methyl(trifluoromethyl)dioxirane at $-40°$ C. with vitamin $D_2$ or its 3β-acetyl derivative has resulted in a high yield (78–80%) of the corresponding tetraepoxide as a single diastereoisomer having the 5,6(β);7,8(β);10,19(α); 22,23 (pseudo-α) configuration. Curici, et al., Oxidation of Natural Targets by Dioxiranes. 4. High Stereo- and Regioselective Conversion of Vitamin $D_2$ to Its (all-R) Tetraepoxide and C-25 Hydroxy Derivative, *J. Am. Chem. Soc.*, 118(45), 11089–11092 (1996). Dioxiranes have also been shown to smoothly oxidize tertiary C—H bonds of saturated spiroketals. Amone, et al., *G. J. Org. Chem.* 1994, 59, 5511.

The cephalostatins and ritterazines comprise a family of forty-five structurally unprecedented marine products with extreme cytotoxicity against human tumors. Outer-Ring Stereochemical Modulation of Cytotoxicity in Cephalostatins, LaCour et al. *Org. Lett.*, 2 (1), 33–36, 2000. The comparison of the biological activity in the cephalostatin and ritterazine series of marine natural products proved cephalostatin 1 to be the most active compound. The very complex and quite unusual bis-steroidal pyrazine structure of this compound, shown below as Formula (I), was first synthesized by the group of P. Fuchs in the United States. T. G. LaCour, C. Guo, S. Bhandaru, M. R. Boyd, P. L. Fuchs. *J. Am. Chem. Soc.* 120, 692 (1998).

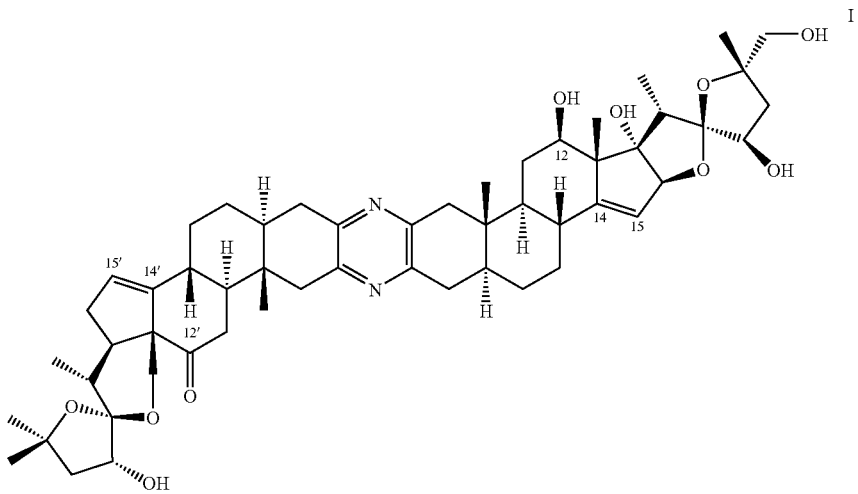

At present, there are forty-five known trisdecacyclic (thirteen rings) pyrazines (cephalostatins and ritterazines) that have been isolated from two very different marine organisms. In addition to the fascinating topology and biosynthetic origin of these compounds, great interest centers on their outstanding potential as antineoplastic agents. Cephalostatin 1 appears to be the most potent inhibitor of the family with an $ED_{50}$ $10^{-7}$–$10^{-9}$ mg/mL in the P38 cell line.

However, it has proven difficult to oxidatively prepare intermediates for synthesis of (−) analogs of the cephalostatin/ ritterazine family of marine natural products using dioxiranes. As illustrated in Scheme 1 of FIG. 1, dioxiranes DMDO and TFDO were unable to affect the desired sequential allylic oxidation of the spiroketal 1. Instead, as illustrated in FIG. 1, efforts to oxidize the spiroketal 1 using DMDO and TFDO led to undesired complex mixtures derived from the epoxy isomers of 4. Neither of the epoxy isomers of 4 undergo useful C—H oxidation using dioxiranes even after extended reaction times.

More generally, while dioxiranes have been used to oxidize natural products, the conditions employed in such oxidations may be somewhat harsh in comparison to the present invention. While in some cases the oxidation may be regioselective (one direction of bond making or breaking occurs preferentially over all other possible directions) and stereospecific, but can lead to undesirable side products. For example, as illustrated in the aforementioned spiroketal example, oxidative use of dioxiranes can lead to the formation of unwanted epoxides.

In contrast to the prior art, the present invention therefore is directed to a stereoselective, preferably a stereospecific oxidative method having wide application in the oxidation of a variety of substrates. Ideally, for application in combinatorial chemistry libraries, such method oxidizes a diverse group of substrates and is chemoselective, preferably chemospecific (i.e., there will be one preferred reaction for a substrate having one of two or more different functional groups). The method is versatile enough to oxidize substrates ranging from branched or unbranched monocyclic compounds such as cyclohexane and ethyl benzene to polycyclic compounds such as the aforementioned spiroketal containing a steroidal functionality.

Because of its chemospecificity, the method avoids unwanted side reactions such as the aforementioned spiroketal epoxidation. Finally, and of great importance in industrial application, the method is catalytic, thereby resulting in a minimal waste stream.

OBJECTS OF THE INVENTION

It is an object of the instant invention to provide a stereospecific oxidative method that will have a wide application in the oxidation of a variety of substrates. Because of this versatility, the method should be useful in combinatorial chemistry libraries.

It is another object of the instant invention to provide a stereospecific oxidative method that will have a wide application in the oxidation of a variety of substrates and which is also chemospecific (i.e., there will be one preferred reaction for a substrate having one of two or more different functional groups).

It is another object of the instant invention to provide a stereospecific and chemospecific oxidative method versatile enough to oxidize a wide variety of hydrocarbons including but not limited to acyclic, monocyclic, bicyclic and polycyclic compounds.

It is a still further object of the present invention to provide a stereospecific and chemospecific oxidative method that is catalytic and thereby results in a minimal waste stream when employed industrially.

SUMMARY OF THE INVENTION

In accordance with the above-stated objects, the invention provides a catalytic, chemospecific and stereospecific method of oxidizing a wide variety of substrates with minimal side reactions. Essentially, the method of the instant invention, under relatively mild reaction conditions, catalytically, stereoselectively (preferably, stereospecifically) and, in the vast majority of cases, chemospecifically inserts oxygen into a hydrocarbon secondary or tertiary C—H bond. Oxidation (oxygen insertion) at a tertiary C—H bond to form an alcohol (and in some cases a hemiacetal) at the tertiary carbon is favored. The stereochemistry of the tertiary carbon is preserved. The method of the instant invention will also oxidize a single secondary C—H bond to form a ketone or two adjacent C—H bonds to form a ring-cleaved dione. For example, the method of the instant invention will oxidize cyclohexane to cyclohexanone and cis decalin to 1,6-cycloundecadienone.

The invention can be used to oxidize a wide variety of hydrocarbons, including but not limited to saturated or unsaturated, substituted or unsubstituted, straight or branched chain alkanes, alkenes or alkynes, and non-hetero aromatic or nonaromatic monocyclic, bicyclic (including fused and bridged bicyclic) and polycyclic compounds. Oxidation in accordance with the method of the instant invention can be done in one-pot reactions or in steps.

The method of the instant invention uses a metallic peroxide to achieve oxidative insertion at secondary or tertiary C—H bonds. In addition, the present invention also achieves oxidation at "active" carbon atoms, i.e., those carbon atoms which occur at a position alpha to an electron withdrawing group such as a olefinic bond, a phenyl group (at a benzylic position), or other conjugated group. As explained in detail hereinafter, one putative reagent useful in the method of the instant invention is tentatively assigned the structure of a neutral dioxoperoxy chromium [VI] ($CrO_2(O_2)$), which undergoes C—H oxidation with retention of stereochemistry. The method of the instant invention favors oxidation of tertiary C—H bonds by insertion of the peroxy oxygen to form an alcohol or hemiacetal at the tertiary carbon. (The tertiary carbon H can be considered as an active hydrogen.) Oxidative reactions in accordance with the method of the instant invention occur at a temperature of about −50° C. to about 0° C., with reactions at a temperature range of −50° C. to −20° being preferred, and reactions at around −40° C. being particularly selective and most preferred. Preferably, oxidation in accordance with the method of the instant invention occurs under a positive pressure of an inert gas such as argon. Reaction times for the method of the instant invention can range from about thirty minutes to around two hours or more. Catalytic yields based on one equivalent of C—H substrate can be as high as 95% or more.

Without being limited by way of theory, as described in detail hereinafter, Cr [VI], a highly electronegative species, catalyzes the insertion of a peroxy oxygen into a C—H bond. Without in any way intending to limit the scope of the invention disclosed and claimed herein, a putative mechanism for this oxidation is akin to dioxirane insertion, except that oxidation by the method of the instant invention occurs under milder reaction conditions. In fact, the method of the instant invention exhibits a selectivity, mildness and yield greater than that of the best available dioxirane process.

For example, in one embodiment of the instant invention, catalytic reaction of spiroketal 1 in the presence of $CrO_2(O_2)$ at −40° C. formed epoxy alcohol 3 by oxygen insertion at tertiary carbon 16 (numbering only the five ring steroidal portion of 1 and designating the tetrahydrofuran ring oxygen as 1, the spirocyclic common carbon as 2, etc.) to form a hemiacetal at $C_{16}$.

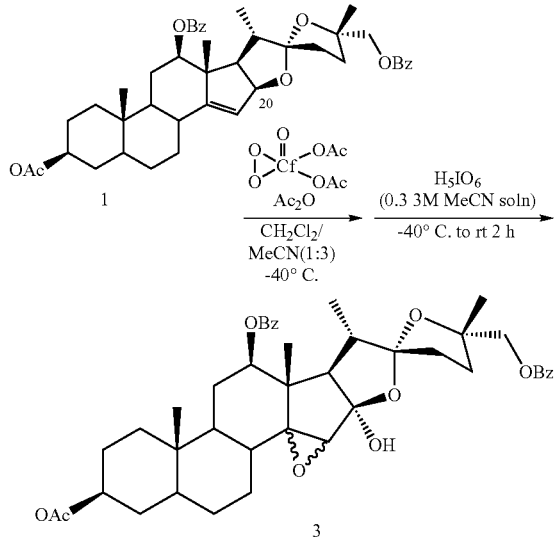

As illustrated by the above reaction, the method of the instant invention chemospecifically and stereoselectively oxidized the tertiary ($C_{16}$) C—H bond in the presence of a remote olefin (alkene) without the formation of unwanted epoxides. Significantly, $CrO_2(O_2)$ appears to be the first reagent capable of oxidation of a C—H bond in the presence of a remote olefin without concomitant epoxidation. The method of the instant invention has therefore proven useful in the synthesis of intermediates appropriate for preparation of hyperactive analogs of the cephalostatin/ritterazine family of marine natural products comprised of epoxyalcohol 3.

As discussed, while oxidation of a tertiary C—H is favored, the method of the instant invention will also chemospecifically oxidize a single secondary C—H to form a ketone or two adjacent tertiary C—H bonds to form a ring-cleaved dione. For example, the invention has been used to catalytically and chemospecifically oxidize: (i) ethyl benzene to acetophenone; and (ii) cyclohexane to form cyclohexanone and cis-decalin to form 1,6-cyclohexanedione.

In one embodiment of the instant invention, a hydrocarbon containing one or more tertiary or secondary C—H bonds is oxidized at one or more of those bonds by reaction with a co-oxidant such as periodic acid or tetrabutylammonium periodate and a highly electronegative oxidant such as chromium trioxide ($CrO_3$) or chromoyl diacetate ($CrO_2(OAc)_2$) at around $-50°$ C. to around $0°$ C. in the presence of one or more anhydrous (non-aqueous) solvents such as acetonitrile ($CH_3CN$) or methylene chloride ($CH_2Cl_2$), preferably a non-polar solvent or a mixture of a polar solvent and non-polar solvent, even more preferably a mixture of acetonitrile and methylene chloride. This reaction is catalytic and stereospecifically and chemospecifically oxidizes tertiary C—H bonds or one or more secondary C—H bonds.

Without in any way intending to limit the scope of the instant invention as claimed herein, the following Scheme 2 illustrates one possible mechanism by which $CrO_3$ selectively and catalytically oxidizes a tertiary C—H ($CR_3$) in accordance with the instant invention. The intermediate chromoylperiodate $A_1$ (or analog $A_2$) may be formed by reaction of $CrO_3$ $SM_1$ (or chromoyl diacetate $SM_2$) via addition of 'anhydrous' $HIO_4$. Formation of the putative peroxy intermediates $R_{1,2}$, followed by insertion to the hydrocarbon C—H bond may yield Cr [VI] compounds $C_1$ and $C_2$ which in turn may decompose to $SM_1$ and $SM_2$, the precatalysts

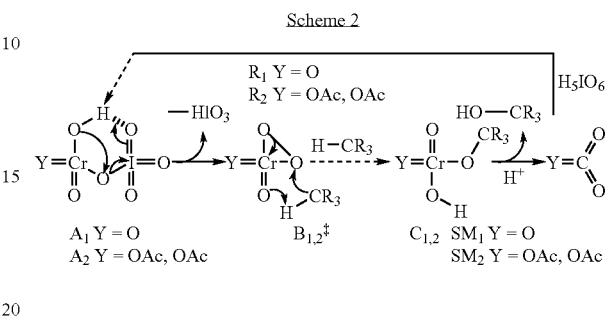

BRIEF DESCRIPTION OF THE DRAWINGS

FIG. 1 also illustrates the actual formation of unwanted epoxy isomers when dioxiranes DMDO and TFDO are used to attempt to allylically oxidize spiroketal 1 to epoxyalcohol 3.

DETAILED DESCRIPTION OF THE INVENTION

Figure 1:
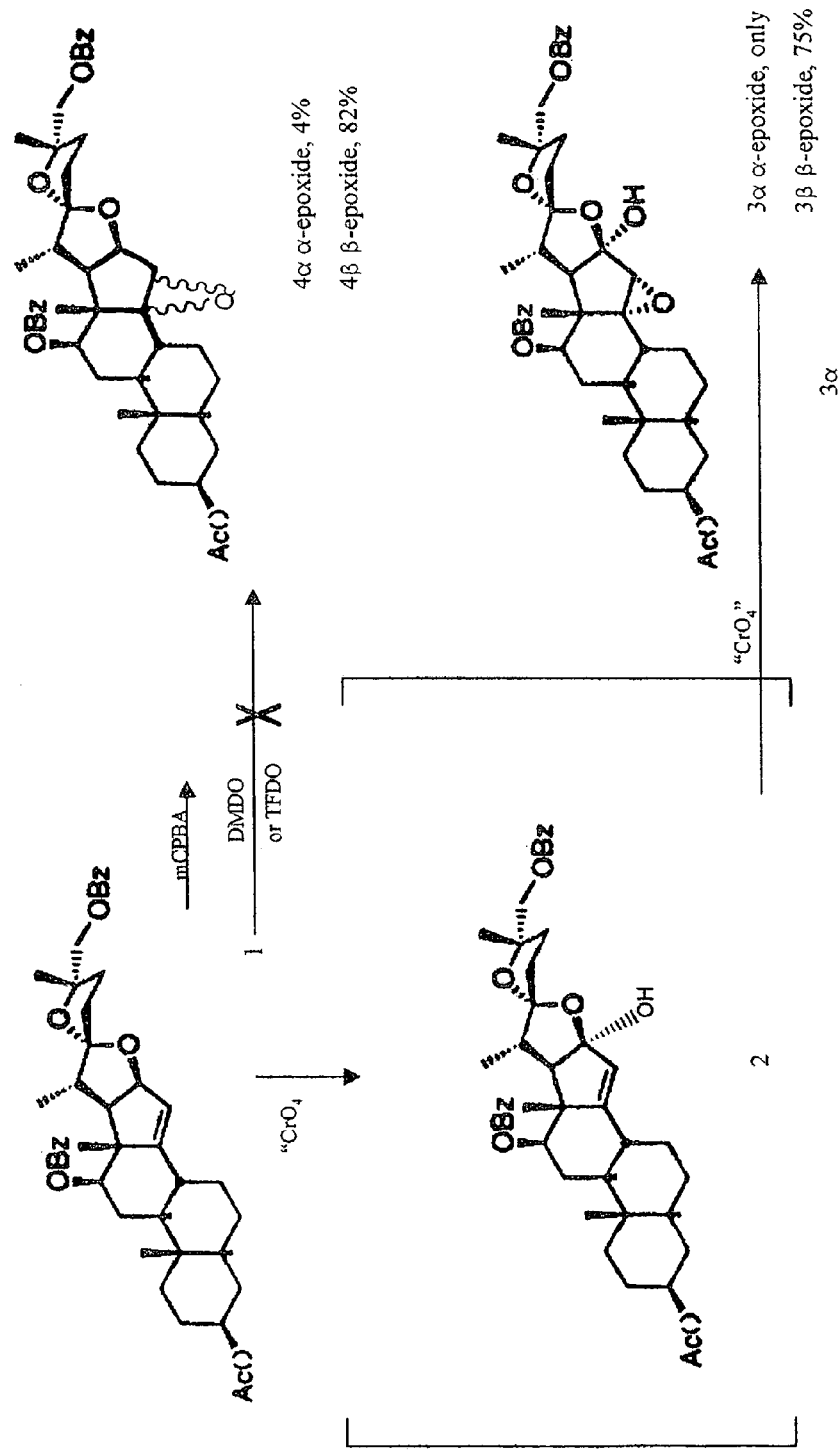
FIG. 1 illustrates a theoretical sequential allylic oxidation of olefin 1 to hemiacetal 2 followed by directed epoxidation to epoxide 3α.
Figure 2:
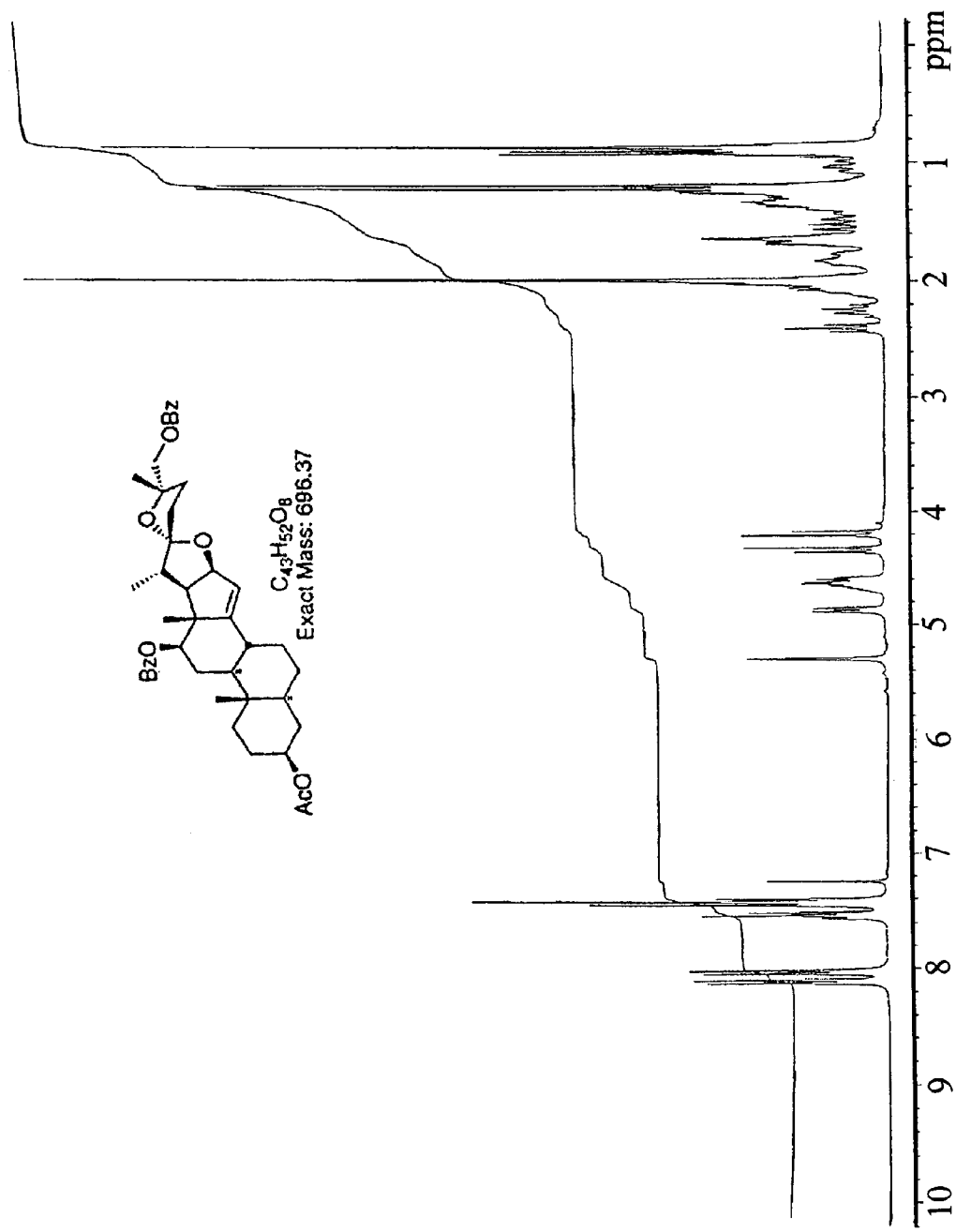
FIG. 2 illustrates proton NMR spectra with superimposed integral for $\Delta^{14}$-spiroketal 1.
Figure 3:
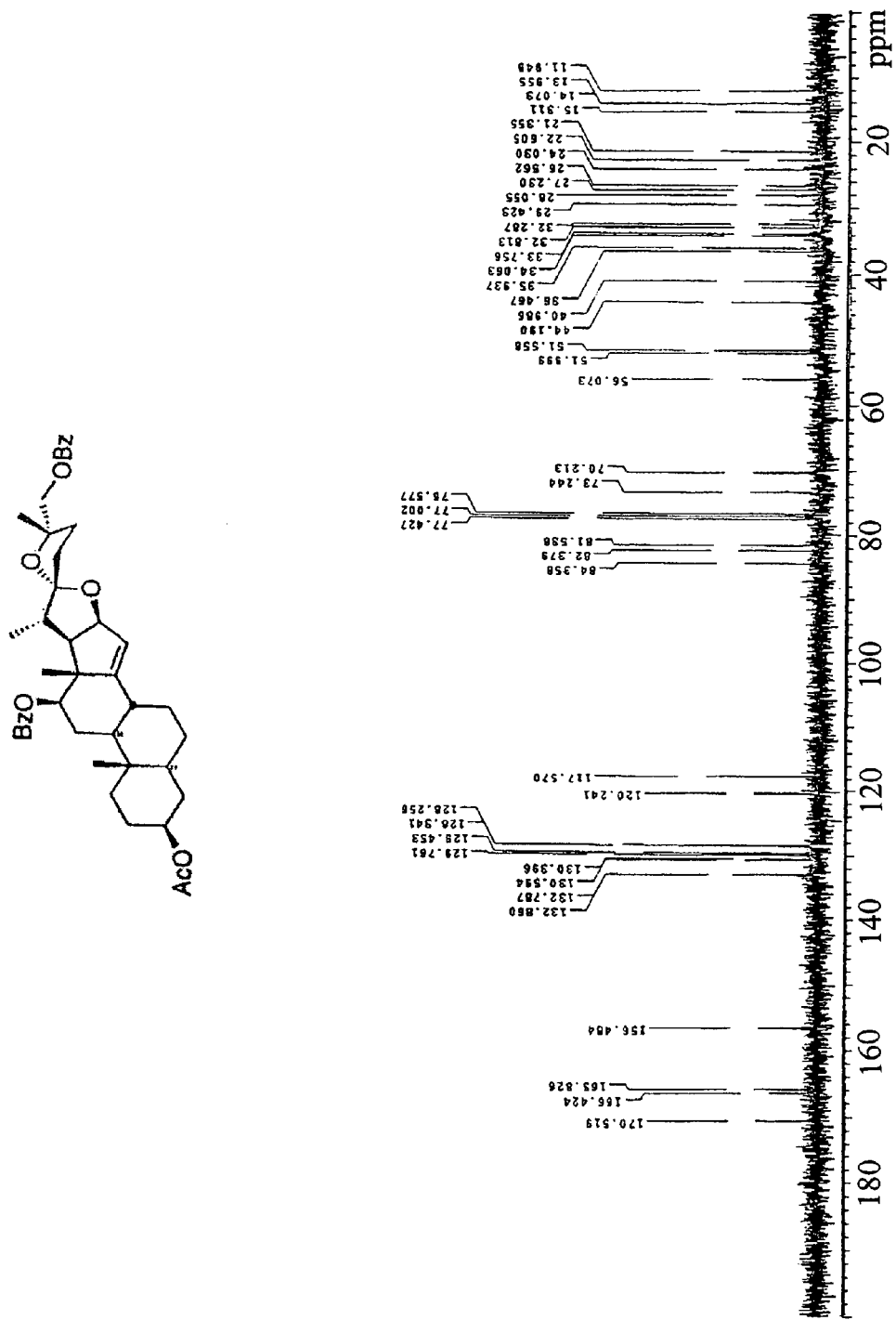
FIG. 3 illustrates proton NMR spectra for $\Delta^{14}$-spiroketal 1.
Figure 4:
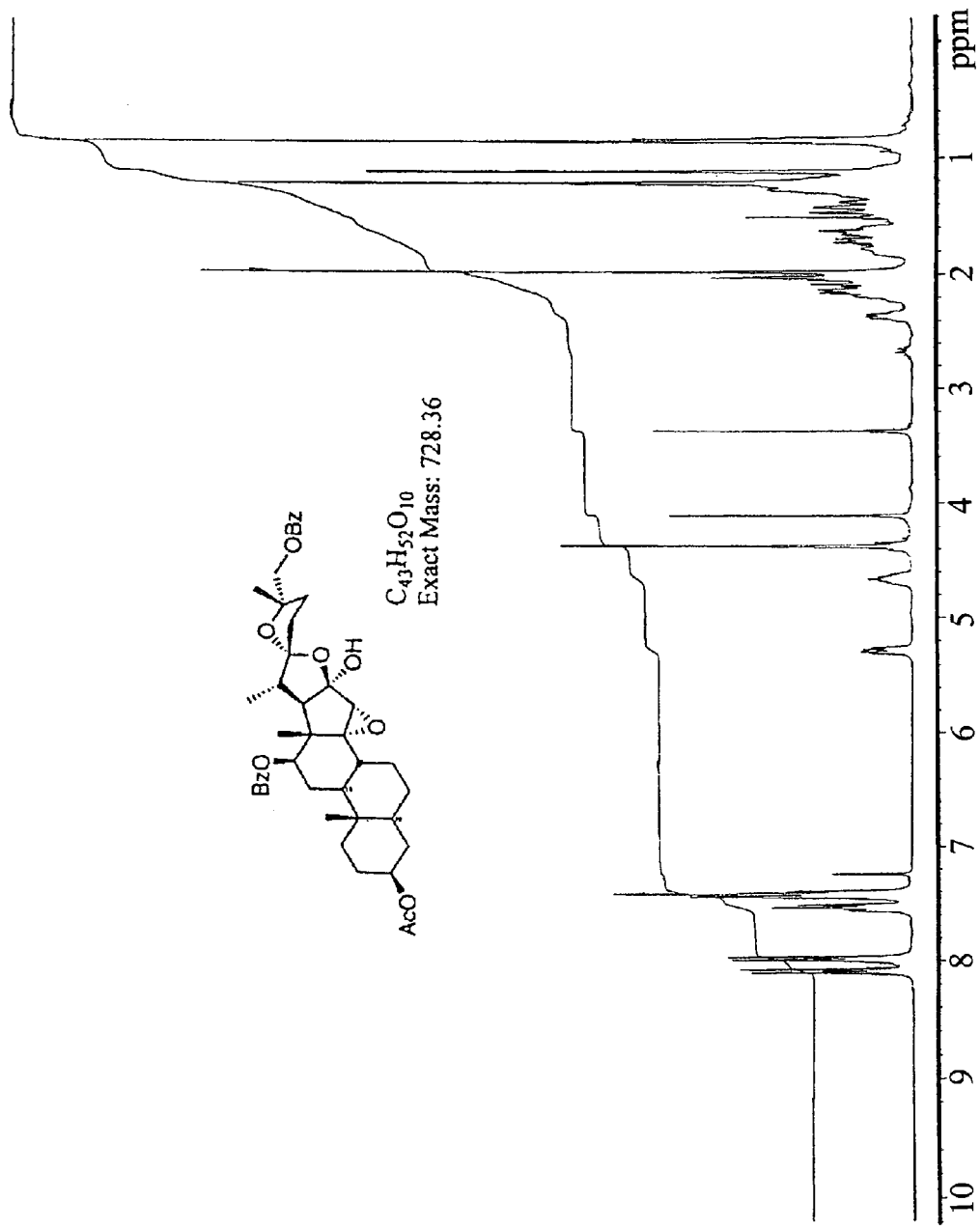
FIG. 4 illustrates proton NMR spectra with superimposed integral for epoxy alcohol 3α.
Figure 5:
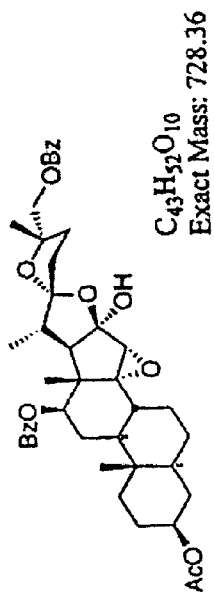
FIG. 5 illustrates proton NMR spectra for epoxy alcohol 3α.
Figure 5:
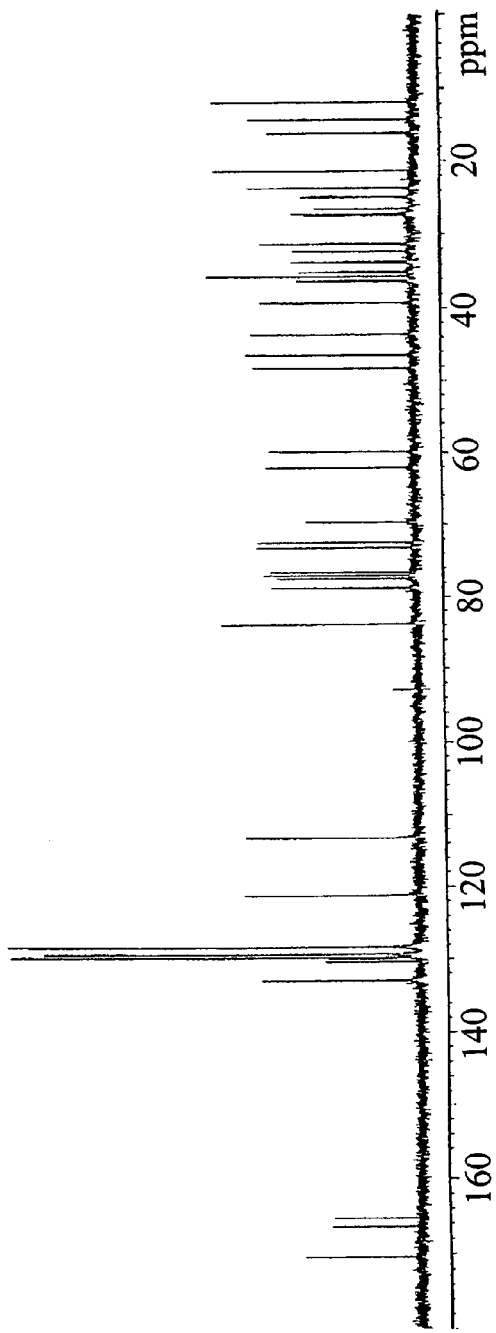
Figure 6:
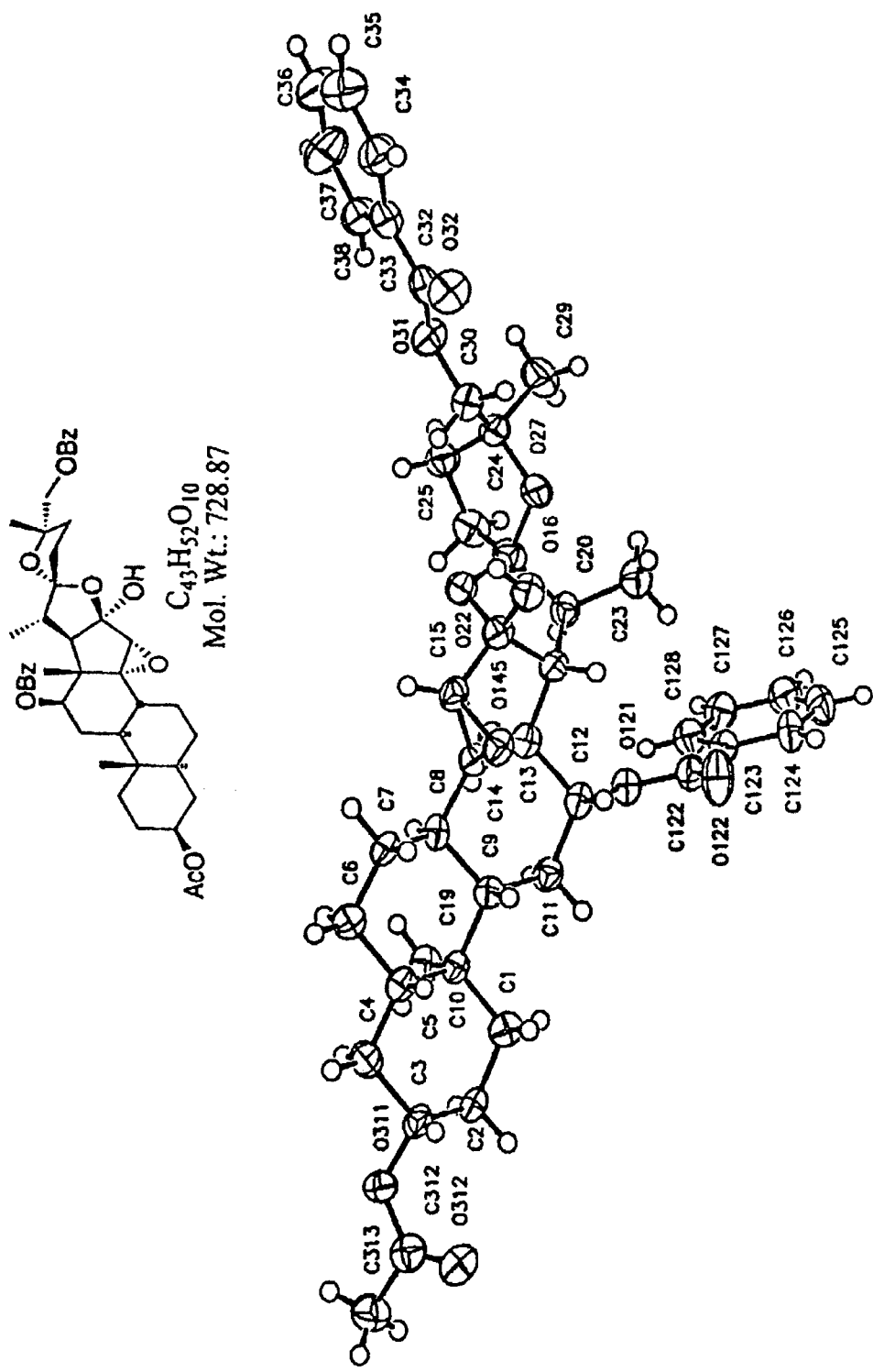
FIG. 6 illustrates a thermal ellipsoid diagram of epoxy alcohol 3α.
Figure 7:
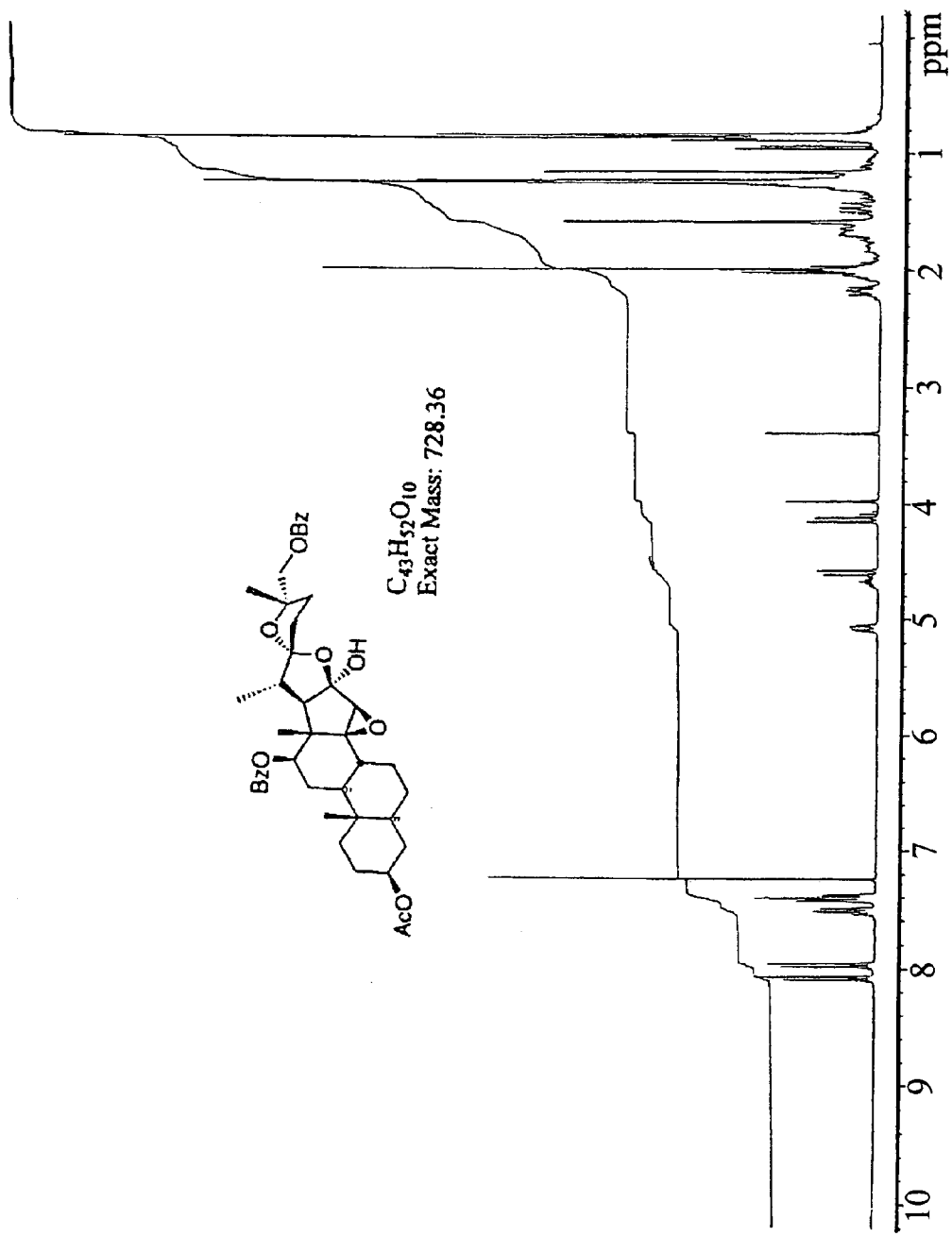
FIG. 7 illustrates proton NMR spectra with superimposed integral for epoxy alcohol 3β.
Figure 8:
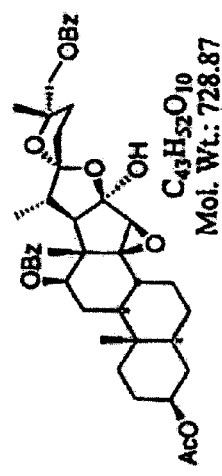
FIG. 8 illustrates proton NMR spectra for epoxy alcohol 3β.
Figure 8:
Figure 9:
FIG. 9 illustrates proton NMR spectra with superimposed integral for epoxy spiroketal 4α.
Figure 10:
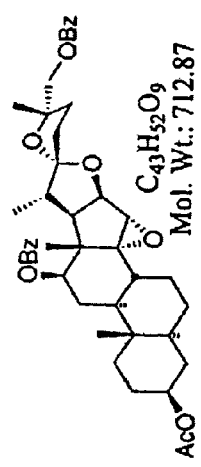
FIG. 10 illustrates proton NMR spectra for epoxy spiroketal 4α.
Figure 10:
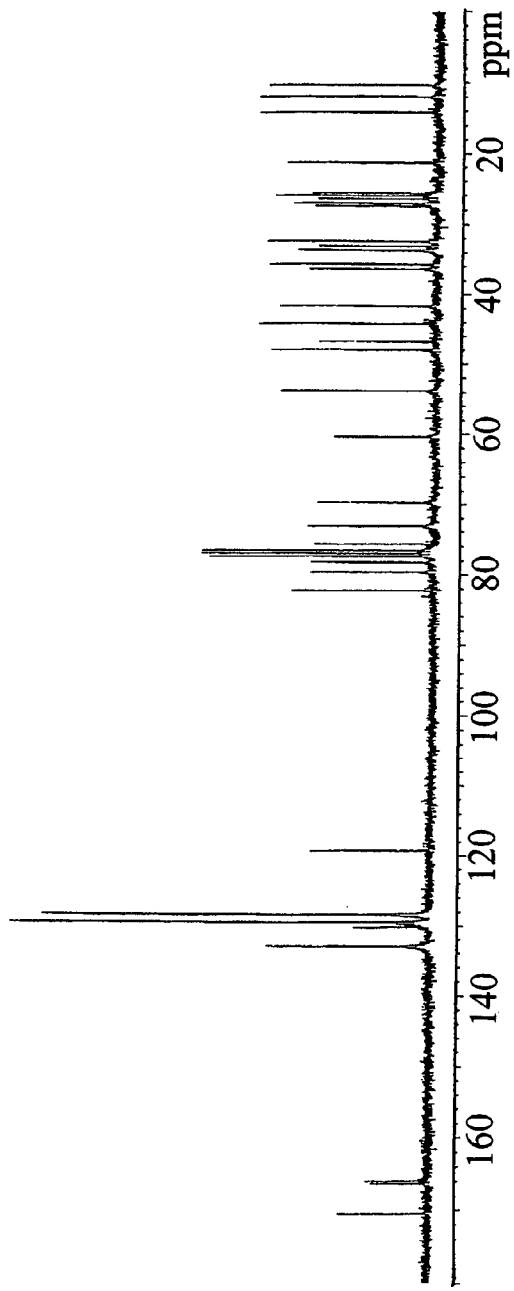
Figure 11:
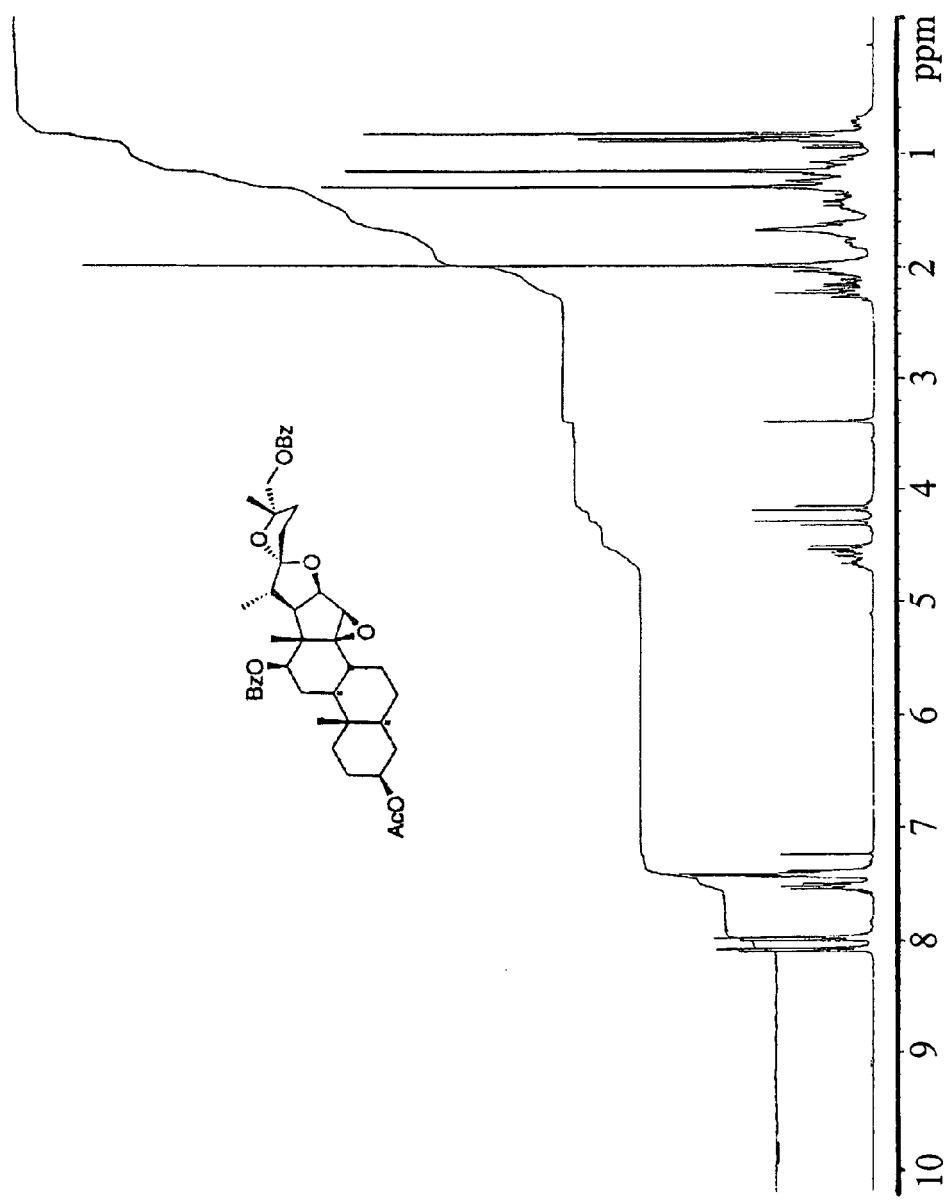
FIG. 11 illustrates proton NMR spectra with superimposed integral for epoxy spiroketal 4β.
Figure 12:
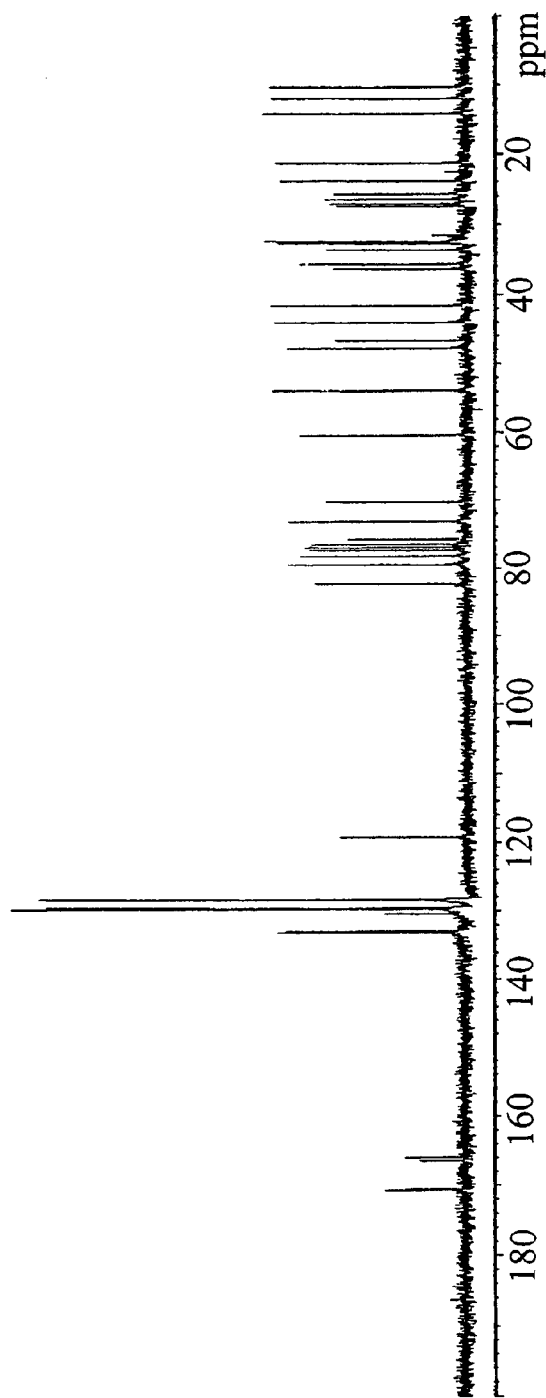
FIG. 12 illustrates proton NMR spectra for epoxy spiroketal 4β.
Figure 13:
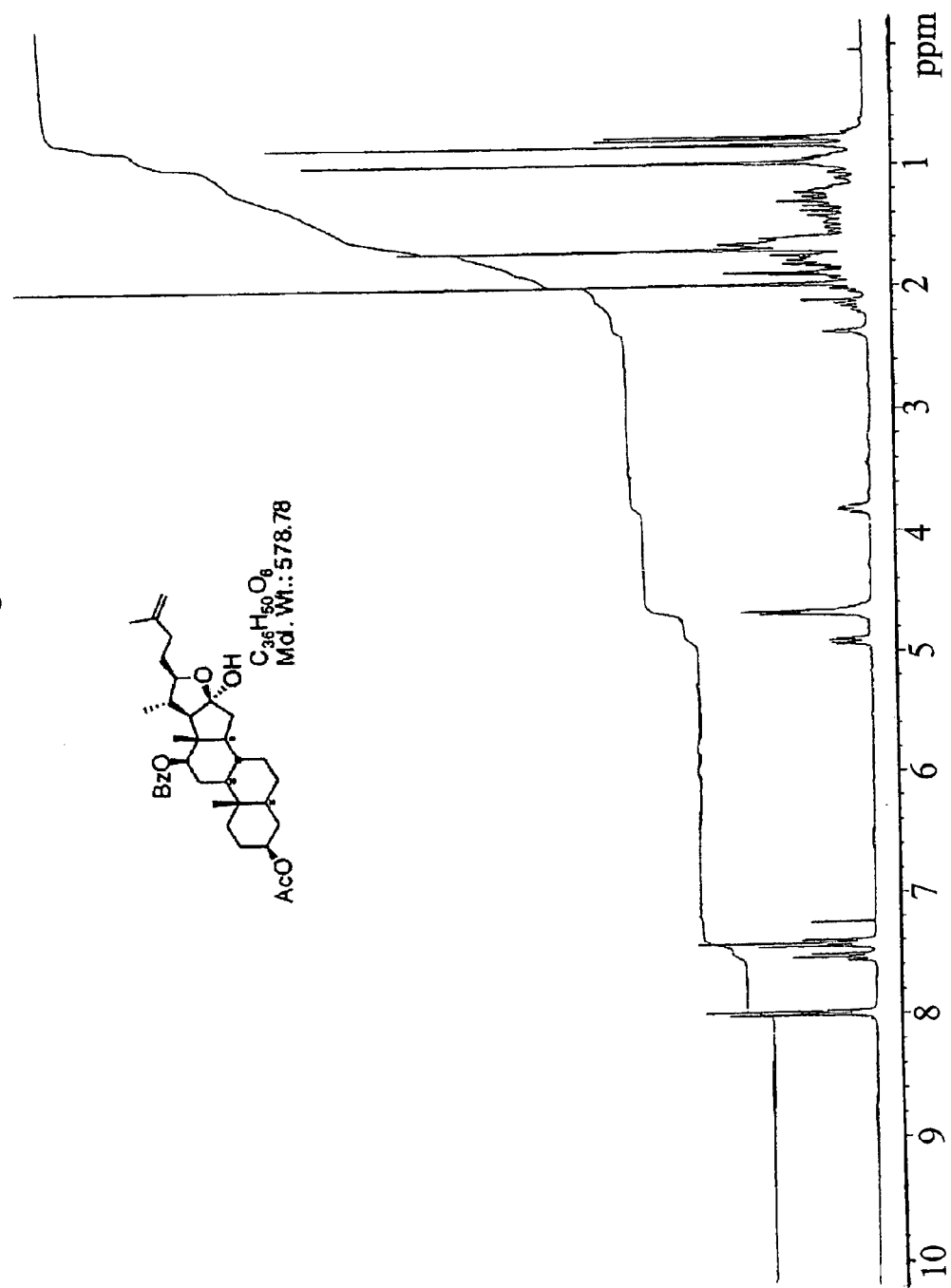
FIG. 13 illustrates proton NMR spectra with superimposed integral for hemiacetal 6.
Figure 14:
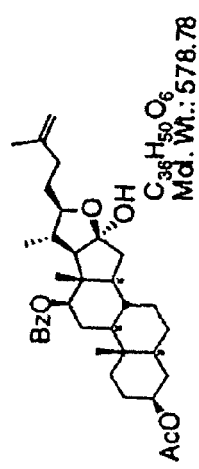
FIG. 14 illustrates proton NMR spectra for hemiacetal 6.
Figure 14:
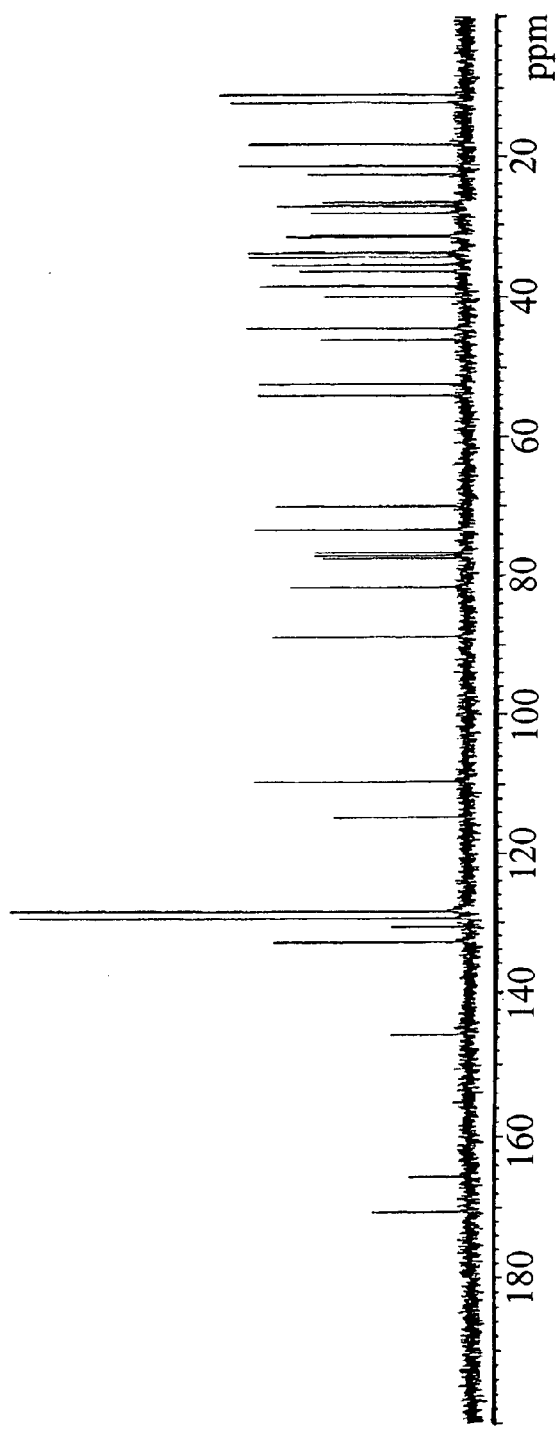
Figure 15:
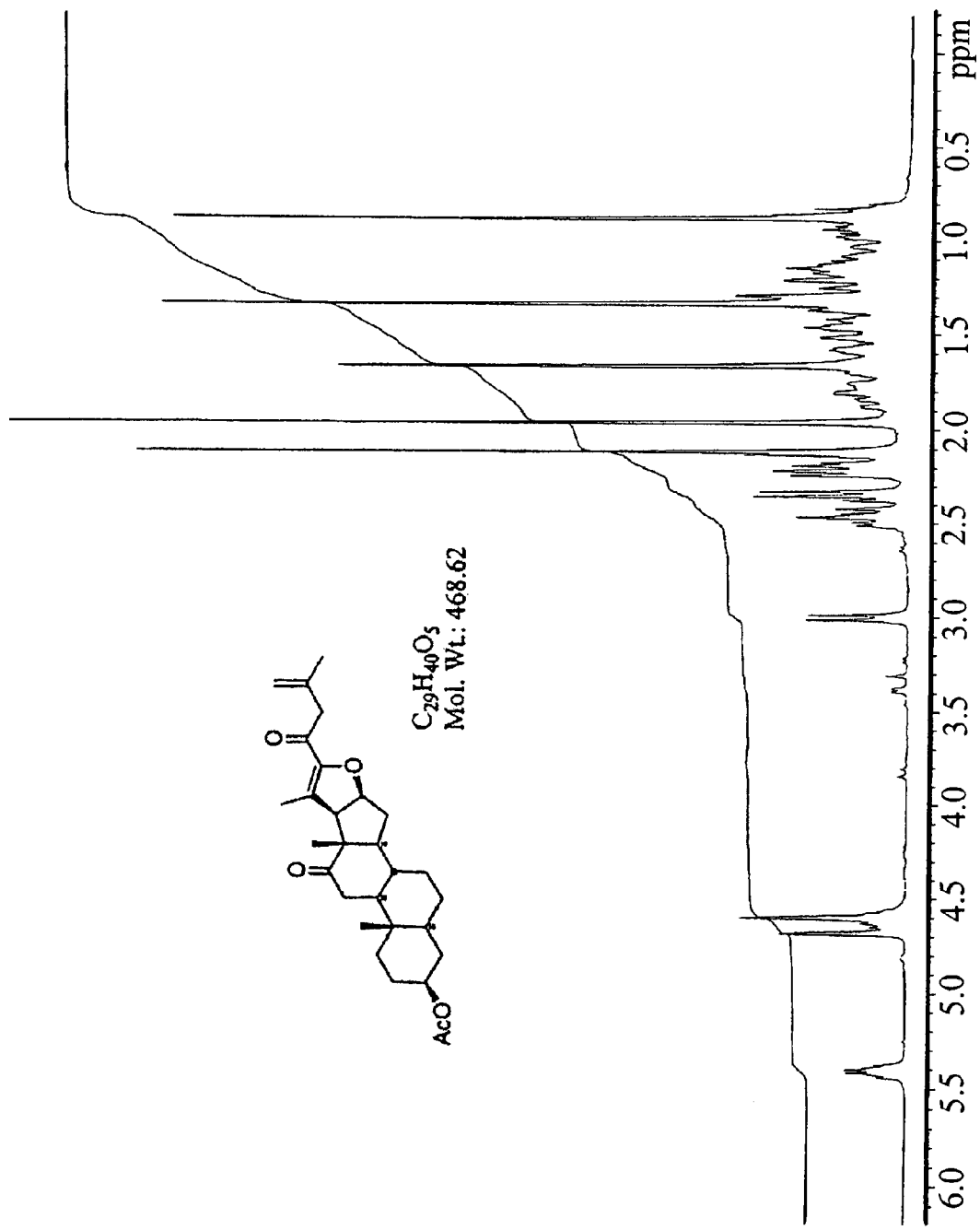
FIG. 15 illustrates proton NMR spectra with superimposed integral for α,β-unsaturated ketone 8.
Figure 16:
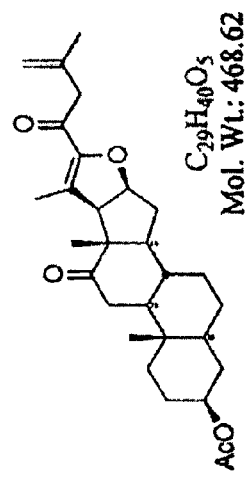
FIG. 16 illustrates proton NMR spectra for α,β-unsaturated ketone 8.
Figure 16:
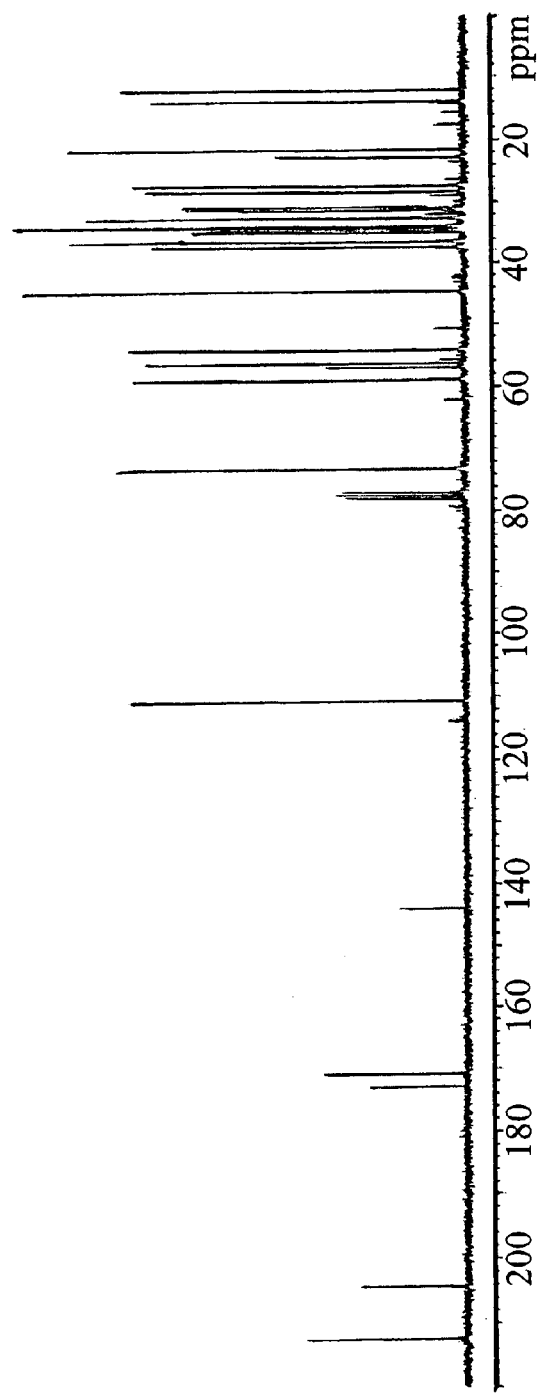
Figure 17:
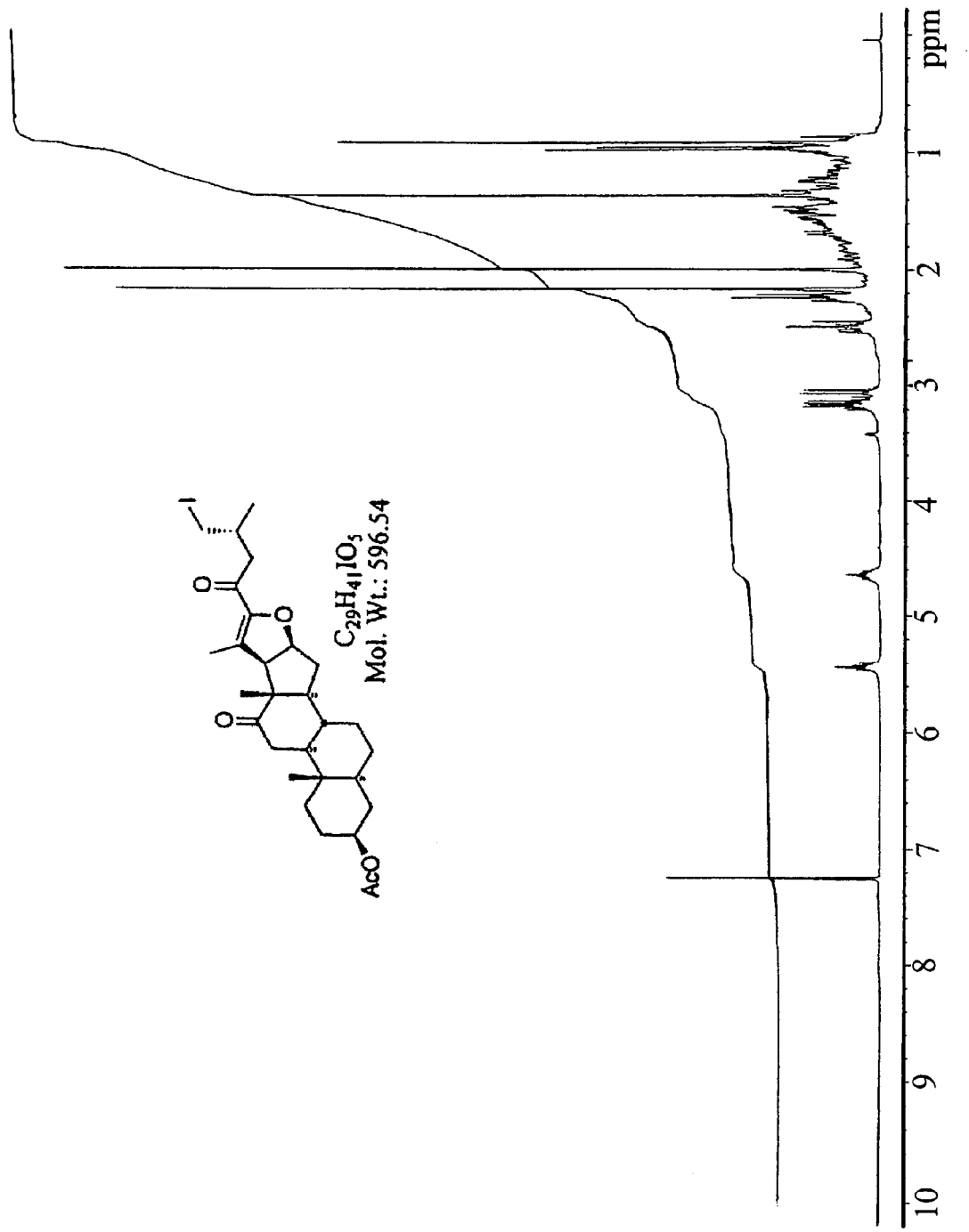
FIG. 17 illustrates proton NMR spectra with superimposed integral for α,β-unsaturated ketone 10.
Figure 18:
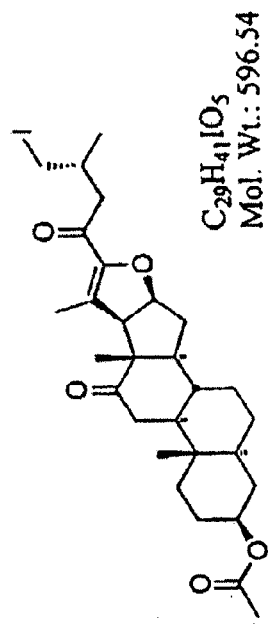
FIG. 18 illustrates proton NMR spectra for α,β-unsaturated ketone 10.
Figure 18:
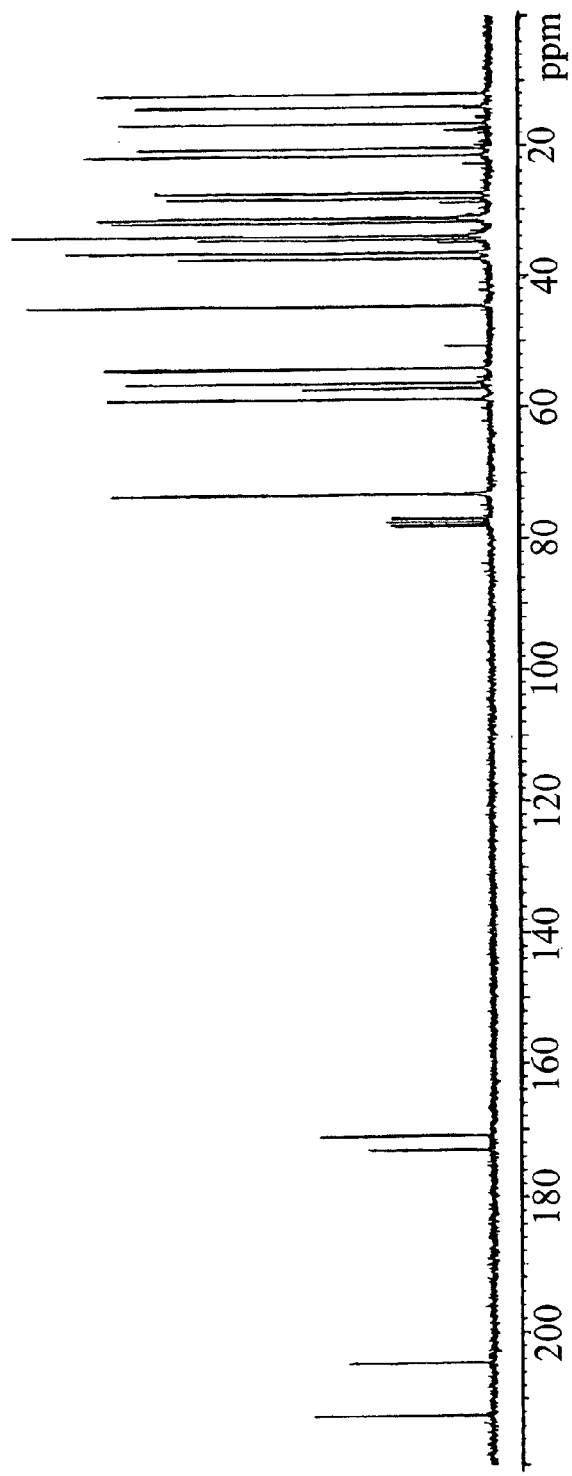

It is to be understood that unless otherwise indicated this invention is not limited to specific reactants, catalyst compositions (including $CrO_2(O_2)$, or synthetic methods. It is also to be understood that the terminology used herein is for the purpose of describing particular embodiments only, and is not intended to be limiting. For example, while the oxidation of particular compounds (substrates) containing secondary or tertiary C—H bonds is discussed throughout, these compounds are intended to be merely representative and not in any way limiting of the many types of compounds that can be oxidized using the method of the instant invention. As another example, while chromoyl diacetate and periodic acid are preferred as, respectively, the oxidant and co-oxidant, such compounds, again, are merely illustrative and not limiting of the reactants with which the present compositions and methods can be used.

As used in this specification and the appended claims, the singular forms "a," "an" and "the" include plural referents unless the context clearly dictates otherwise. Thus, reference to "a solvent" can include mixtures of solvents, "a co-oxidant" includes mixtures of co-oxidants, "a catalyst composition" can includes mixtures of catalyst compositions, and the like.

As used herein, the following terms have the following definitions.

"Optional" or "optionally" means that the subsequently described event or circumstance may or may not occur, and that the description includes instances where said event or circumstance occurs and instances where it does not. For example, the phrase "optionally substituted alkyl" means that a alkyl moiety may or may not be substituted and that the description includes both unsubstituted alkyl and alkyl where there is substitution.

The term "acetal" means a compound in which two ether oxygens are bound to the same carbon. A "ketal" is an acetal derived from a ketone. The terms acetal and ketal may be used synonymously in many instances within context in the description of the present invention.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms.

"Substituted alkyl" refers to alkyl substituted with one or more substituent groups, and the terms "heteroatom-containing alkyl" and "heteroalkyl" refer to alkyl in which at least one carbon atom is replaced with a heteroatom preferably selected from N, S, O, P or Se, preferably N, S or O. The term "alkylene" refers to fully saturated hydrocarbon radicals which are divalent, in contrast to alkyl groups, which are monovalent.

The term "alkenyl" as used herein refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. The term "alkenylene" refers to a divalent alkenyl group.

The term "alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through an ether linkage; that is, an "alkoxy" group may be represented as —O-alkyl where alkyl is as defined above. A "lower alkoxy" group intends an alkoxy group containing one to six, more preferably one to four, carbon atoms.

The term "allenyl" is used herein in the conventional sense to refer to a molecular segment having the structure —CH=C=CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. In particular embodiments, aryl substituents have 1 to about 200 carbon atoms, typically 1 to about 50 carbon atoms, and preferably 1 to about 20 carbon atoms. "Substituted aryl" refers to an aryl moiety substituted with one or more substituent groups, and the terms "heteroatom-containing aryl" and "heteroaryl" refers to aryl in which at least one carbon atom is replaced with a heteroatom.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

"Chemospecific" means a reaction that is 100% chemoselective. "Chemoselective" means preferential reaction of a chemical reagent with one of two or more different functional groups (i.e., greater than 50%, more preferably greater than about 75%, even more preferably, greater than about 90%). A reagent has a high chemoselectivity if reaction occurs with only a limited number of different functional groups. For example, sodium tetrahydroborate is a more chemoselective reducing agent than is lithium tetrahydroaluminate. The concept has not been defined in more quantitative terms. The term is also applied to reacting molecules or intermediates that exhibit selectivity towards chemically different reagents.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" refers to a molecule or molecular fragment in which one or more carbon atoms is replaced with an atom other carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

By "substituted" as in "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

"Allylic oxidation" means oxidation of an allylic compound by replacing at least one allylic hydrogen(s) with oxygen or an oxygen-containing group. Allylic compounds are any organic compound incorporating the structure RC=C$^2$H—C$^3$H$_n$ within the molecule, wherein n is 1, 2 or 3. Hydrogen atoms attached to the C$^1$ and C$^2$ carbon atoms are referenced as vinylic hydrogen. Hydrogen atoms attached to the C$^3$ carbon atoms are referenced as allylic hydrogens.

"Active C—H" means a labile or acidic hydrogen that will readily leave a molecule and act as an acid. For example, in the present invention, hydrogens on carbon atoms alpha to phenyl, olefinic or other conjugated groups are active. In addition, alcohols and carboxylic acids have active hydrogens.

"Alpha" ("α") to a group means adjacent to that group. Alpha may also refer to the configuration of a substituent about a carbon group which is below a plane of reference.

"Beta" ("β") to a group means one carbon removed from that group. Beta may also refer to the configuration of a substituent about a carbon group which is above a plane of reference.

"Benzylic C—H group" means a C—H adjacent (α) to a benzene ring or substituted benzene ring.

"Dioxiranes" are compounds of the structure

where $R_1$ and $R_2$ can be, e.g., H, F, CH$_3$ or CF$_3$. Dioxiranes are conveniently prepared from ketones by treatment with Caroate and isolated as ketone solutions by distillation. When the substrate and oxidized product tolerates aqueous conditions, the in-situ procedure is preferred. A large variety of electron-rich and electron-poor substrates may be oxyfunctionalized by DMD, which includes epoxidations (π bonds), hydroxylations (σ bonds) and hetero-atom oxidations (lone pairs). Dioxiranes are valuable oxidants in organic synthesis and include DMDO and TFDO.

"Hemiacetal" means compounds having the general formula R$_2$C(OH)OR' (R' does not equal H). The term hemiacetal and "hemiketal" are, in many instances used synonymously in describing the present invention.

"Insertion" means a chemical reaction or transformation of the general type:

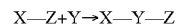

in which the connecting atom or group Y replaces the bond joining the parts X and Z of the reactant XZ. An example is insertion of a peroxy oxygen into a tertiary C—H bond illustrated in the preceding Scheme 2.

"Oxidant" and "co-oxidant" mean a compound that gives up oxygen readily, removes hydrogen from another compound, or attracts electrons. Oxidants as used herein include Cr[VI] species such as CrO$_3$ and chromoyl diacetate. Chromoyl diacetate (CrO$_2$(OAc)$_2$) is a preferred oxidant. Co-oxidants include but are not limited to periodic acid, tetrabutylammonium periodate, hydrogen peroxide, t-butyl hydroperoxide, diacyl peroxides, bis-trimethylsilylperoxide (TMSOOTMS), peroxydisulfate and persulfate.

Periodic acid and tetrabutylammonium periodate are preferred co-oxidants for use in the present invention.

"Regioselective" reaction means a reaction in which one direction of bond making or breaking occurs preferentially over all other possible directions. Reactions are termed completely (100%) regioselective if the discrimination is complete, or partially (x %), if the product of reaction at one site predominates over the product of reaction at other sites. The discrimination may also semi-quantitatively be referred to as high or low regioselectivity.

"Sigmatropic rearrangement" means a reaction in which a σ bond migrates over a number of atoms in a molecule. For example, a [3,3] sigmatropic reaction means that each end of a σ bond migrates over 3 atoms.

"Spiroketals" are spirocyclic compounds (two rings having a single shared carbon atom) and are a prevalent structure in a wide number of biologically important natural products. A spiroketal contains an acetal group derived from a ketone. The use of spiroketals as lead structures is a potentially promising area for investigation because recent literature reports have shown that simplified compounds exhibit interesting pharmacological effects, such as tubulin modulation and cytotoxicity against tumor cell lines.

A reaction is termed "stereospecific" if starting materials differing only in their configuration are converted into stereoisomeric products. According to this definition, a stereospecific process is necessarily stereoselective but not all stereoselective processes are stereospecific. Stereospecificity may be total (100%) or partial. The term is also applied to situations where reaction can be performed with only one stereoisomer. For example the exclusive formation of trans-1,2-dibromocyclohexane upon bromination of cyclohexene is a stereospecific process, although the analogous reaction with (E)-cyclohexene has not been performed.

"Secondary C—H bond" means a C—H bond where the C is attached to two other carbons.

"Tertiary C—H bond" means a C—H bond where the C is attached to three other carbons.

The present invention relates to a method of oxidizing a hydrocarbon comprising reacting the hydrocarbon in an anhydrous solvent (preferably, a nonpolar solvent or a mixture of a polar and nonpolar solvent) with a chromium [VI] oxidant and a co-oxidant at a reaction temperature of between about −50° C. to about 0° C., thereby catalytically and chemospecifically oxidizing the hydrocarbon: (i) substantially stereospecifically at a tertiary carbon to form a tertiary alcohol or hemiacetal, or (ii) at a one or more secondary carbons to form a ketone or dione, or (iii) at cis tertiary CH groups to form a ring-cleaved dione.

In a further aspect of the present invention, in the present method (i) the chromium [VI] oxidant is selected from the group consisting of $CrO_3$, chromoyl diacetate, chromoyl chloride, chromoyl bistrifluoroacetate, chromoyl bistriflate, and chromoyl bis t-butylester, (ii) the co-oxidant is selected from the group consisting of periodic acid, tetrabutylammonium periodate, hydrogen peroxide, t-butyl hydroperoxide, diacyl peroxides, TMSOOTMS, peroxydisulfate and persulfate, and (iii) the solvent is selected from the group consisting of acetic acid, acetonitrile, methylene chloride and mixtures, thereof.

In a further preferred aspect of the invention, the chromium [VI] oxidant is chromoyl diacetate, the co-oxidant is periodic acid or tetrabutylammonium periodate, the solvent is a mixture of acetonitrile and methylene chloride, the reaction time is from about thirty minutes to about three hours, and the reaction takes place under a positive pressure of inert gas.

In another aspect of the present invention, in the method of the present invention, a mixture solution of the hydrocarbon, chromium [VI] oxidant and an aqueous solvent is formed and a mixture of co-oxidant and aqueous solvent is added to the mixture solution.

In a further aspect of the present invention, the mixture solution of hydrocarbon, chromium [VI] oxidant and anhydrous solvent comprises $CrO_3$, methylene chloride and acetonitrile and the mixture of co-oxidant and an anhydrous solvent comprises periodic acid and acetonitrile. Alternatively, the mixture solution of hydrocarbon, chromium [VI] oxidant and anhydrous solvent comprises chromoyl diacetate, methylene chloride and acetonitrile and the mixture of co-oxidant and anhydrous solvent comprises tetrabutylammonium periodate and acetonitrile.

In certain preferred aspects of the present invention, the reaction temperature is preferably approximately −50° C. to approximately −20° C. In a particularly preferred aspect of the present invention, the reaction temperature is approximately −40° C.

The present invention may be applied very broadly to a large number of hydrocarbon compounds. In a number of embodiments of the present invention, the hydrocarbon to be oxidized is preferably a saturated or unsaturated, substituted or unsubstituted, hetero or non-hetero, aromatic or nonaromatic linear, branched or mono, bi- or polycyclic compound.

In other aspects of the present invention, a hydrocarbon tertiary carbon is oxidized to form a tertiary alcohol or hemiacetal or two cis tertiary carbons are oxidized to form a ring-cleaved dione. In still other aspects, a hydrocarbon secondary carbon is oxidized to form a ketone.

In certain preferred aspects of the present invention, the hydrocarbon contains one or more of the following groups: alkyl, cycloalkyl, alkenyl, alkynyl, alkoxy, allenyl, aryl, aralkyl, aralkylene, alkarylene, an epoxide, heteroaryl, haloalkyl, haloalkenyl and haloalkynyl.

In still other aspects of the present invention, the hydrocarbon secondary carbon is contained with an alkoxy group or is a benzylic carbon.

By way of example, in accordance with the instant invention, periodic acid was reacted under a positive pressure of argon gas with chromoyl diacetate ($CrO_2(OAc)_2$) at around −40° C. in acetonitrile ($CH_3CN$) to form an oxidizing solution. This solution catalytically oxidized ethyl benzene in the presence of methylene chloride ($CH_2Cl$) in a reaction time of around two hours to yield acetophenone.

Product yields for this catalytic reaction are set forth in the following Table 1. NMR and mass spectrometry characterizations for the reaction are disclosed in Examples 3 and 4 hereinafter.

TABLE 1

| "Cr'(eq) | $Ac_2O$ (eq) | $H_5IO_6$ (eq) | Conc. (M) | yield |
|---|---|---|---|---|
| 0.1 | 2 | 3.0 | 1 to 0.1 | 87% |
| 0.05 | 1 | 0.5 | 2 to 0.5 | 47% |
| 0.05 | TFAA (2) | 0.5 | 2 to 0.5 | 34% |
| 0.05 | 1 | 1.0 | 2 to 0.3 | 59% |
| 0.05 | 1 | 1.5 | 2 to 0.2 | 69% |
| 0.05 | 2 | 3.0 | 2 to 0.1 | 96% |
| 0.05 | 2 | 3.0 | 2 to 0.2 | — |

Initial oxidations of ethyl benzene were carried out with excess $CrO_3$, but the more soluble chromoyl diacetate was found to be a superior oxidant. Other chromium[VI] substrates including chromoyl chloride, chromoyl bistrifluoroacetate, chromoyl bistriflate, and chromoyl bis t-butylester were tested but were found to be inferior to chromoyl diacetate. The premier co-oxidants tested proved to be periodic acid and tetrabutylammonium periodate. Hydrogen peroxide, t-butyl hydroperoxide, diacyl peroxides, TMSOOTMS, peroxydisulfate, and persulfate proved to be inferior co-oxidants when compared to periodic acid and tetrabutylammonium periodate.

Of considerable significance is that C—H oxidation occurred at about −40° C., and the reaction is catalytic in chromium. Reaction mixtures found to be deficient in co-oxidant at first exhibited a brownish-orange color, but then rapidly turned green and ceased oxidation. Addition of excess periodic acid re-established both the brown-orange color and the oxidative process. Both excess periodic acid and acetic anhydride were found to be required for optimal yield of acetophenone from ethyl benzene.

An expanded series of substrates listed in Table 2 below were oxidized in accordance with the same procedure. The results of such oxidation revealed several aspects of the method of the instant invention. The method is stereospecific and retains the stereochemistry of the C—H bond oxidized, as is evident from Table 2, entries 6–9 and 10. While a second oxidation can yield a cis-diol, periodate effects rapid oxidative cleavage, as evidenced by table 2, entries 5 and 10. While substantially preferred, oxidation is not restricted to tertiary C—H bond. For example, cyclohexane and its perdeuterio analog are oxidized to cyclohexane ($k_H/k_D$=2.5), similar to the TFDO oxidation of cyclohexane ($k_H/k_D$=2.2). (Attempts at tapping secondary alcohol intermediates using excess trifluoroacetic anhydride were not successful.) By comparison to most C—H oxidation studies, which typically employ an excess of substrate, all the yields reported herein are based upon one equivalent of C—H.

TABLE 2

| Entry | Substrate (X = H) | Product (% yield)[a] | | | |
|---|---|---|---|---|---|
| | | Stoichiometric[b] | | catalytic[c] | |
| 1 | [structure] | X=OH | 68 | | |
| 2 | [structure] | X=O | 57[d] | X=O | 41 |
| 3 | [structure with $D_{10}$] | X=O | 23[d] | | |
| 4 | [structure] | | | X=OH | 65[e] |
| 5 | [structure] | [diketone structure] | 43 | [diketone structure] | 48 |
| 6 | [structure] | | | X=OH | 54 |
| 7 | [structure] | | | X=OH | 73 |
| 8 | [structure] | | | X=OH | 65 |
| 9 | [decalin structure] | X=OH | 69 | X=OH | 51 |
| 10 | [decalin structure] | X=OH | 84 | [diketone structure] | 56 |

TABLE 2-continued

| Entry | Substrate (X = H) | Product (% yield)[a] Stoichiometric[b] | | catalytic[c] | |
|---|---|---|---|---|---|
| 11 | 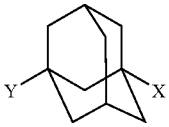 | X=OH, Y=H | 55 | X=OH, Y=H | 86[h] |
|  |  |  |  | X,Y=OH | <2[h] |
| 12 | 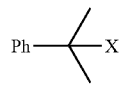 | X=OH | 92 | X=OH | 64[f] |
| 13 | 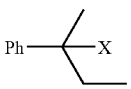 |  |  | X=OH | 89[g] |
| 14 | 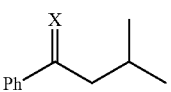 |  |  | X=O | 91 |
| 15 | Ph₃CX | X=OH | 97 | X=OH | 95 |
| 16 | 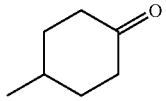 | NR |  | NR |  |

[a]isolated yield;
[b]CrO₃ (3eq), Bu₄NIO₄ (3eq), −40° C. 10 min;
[c]CrO₂(OAc)₂ (5 mol %), H₅IO₆ (3eq), −40 to 0° C. 2h;
[d]−20° C. 1h;
[e]prolonged reaction (12h) gave tertiary acetamide (82%, X=NHAc);
[f]amide (19%, X=NHAc) and acetophenone (10%) isolate;
[g]amide (4%, X=NHAc) and acetophenone (3%) formed;
[h]H₅IO₆ (10 eq), −40 to 0° C. 2h Reaction of substrates bearing tertiary amide or lactam functionalities revealed that amides, including DMF, prevented oxidation, possibly because the amides or lactams served as non-dissociable ligands. Trichloroacetonitrile and benzonitrile did not facilitate the reaction, possibly because of their inability to dissolve the periodic acid.

The method of the instant invention has also been used to stoichiometrically oxidize spiroketal 1 to produce epoxyalcohol 3 in 66% yield along with 26% of the C-22 spiroketal isomer, presumably due to acid-catalyzed isomerization.

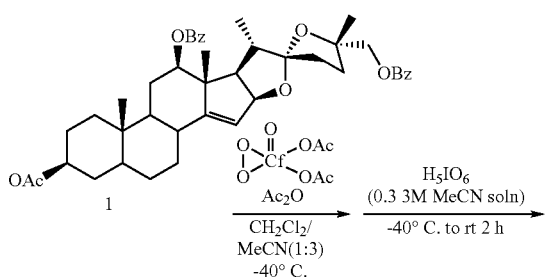

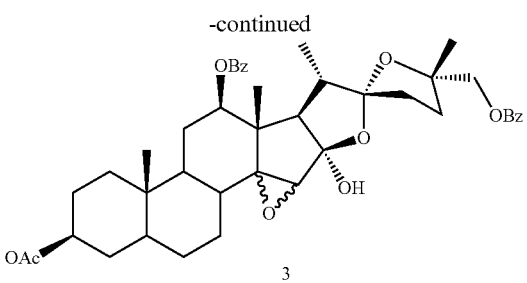

Monitoring the above reaction by NMR provided no evidence of the formation of intermediates 2 or epoxyspiroketal 4 depicted in reaction Scheme 1 of FIG. 1. Evidence in support of the fact that C—H oxidation precedes epoxidation in the above reaction is seen in the Cr oxidation of epoxyspiroketal 4β depicted in FIG. 1 which requires more forcing conditions (−10° C., 1 h) to stereospecifically generate epoxyalcohol 3β. NMR and mass spectrometry characterizations for the above reaction are provided hereinafter in Example 4

Additionally, in accordance with the reaction below, the method of the instant invention has been used to affect the novel chemospecific oxidation of ketone 5 to hemiacetal 6 and allylic oxidations of enol ethers 7 and 9 to form α,β-unsaturated ketones 8 and 10. These reactions were found to occur without any competitive oxidation. This reaction may occur via initial attack of C-16 with the peroxy moiety of "CrO$_4$" followed by [3.3] sigmatropic rearrangement and rapid oxidation of the incipient allylic alcohol.

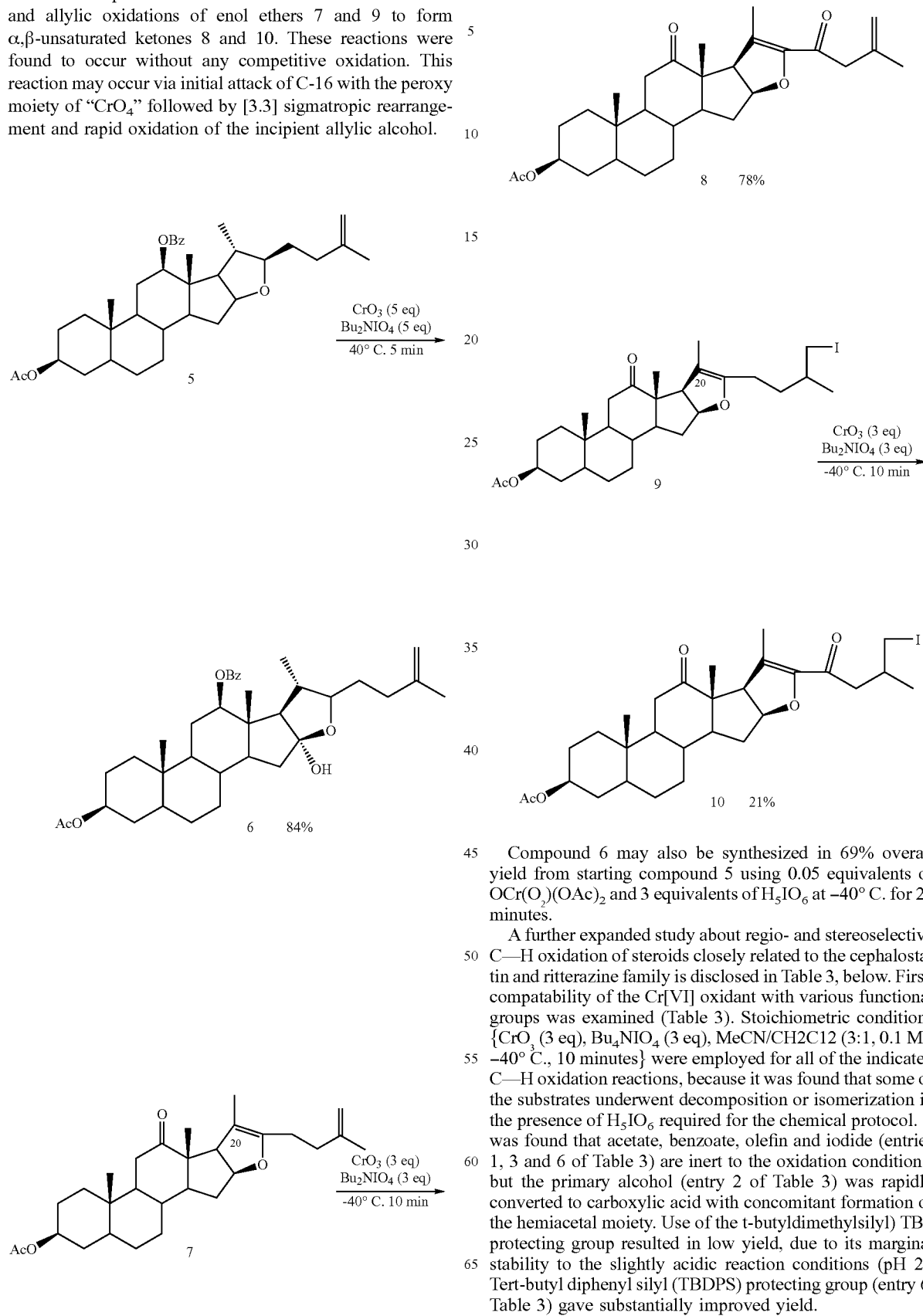

Compound 6 may also be synthesized in 69% overall yield from starting compound 5 using 0.05 equivalents of OCr(O$_2$)(OAc)$_2$ and 3 equivalents of H$_5$IO$_6$ at −40° C. for 20 minutes.

A further expanded study about regio- and stereoselective C—H oxidation of steroids closely related to the cephalostatin and ritterazine family is disclosed in Table 3, below. First, compatability of the Cr[VI] oxidant with various functional groups was examined (Table 3). Stoichiometric conditions {CrO$_3$ (3 eq), Bu$_4$NIO$_4$ (3 eq), MeCN/CH2Cl2 (3:1, 0.1 M), −40° C., 10 minutes} were employed for all of the indicated C—H oxidation reactions, because it was found that some of the substrates underwent decomposition or isomerization in the presence of H$_5$IO$_6$ required for the chemical protocol. It was found that acetate, benzoate, olefin and iodide (entries 1, 3 and 6 of Table 3) are inert to the oxidation conditions, but the primary alcohol (entry 2 of Table 3) was rapidly converted to carboxylic acid with concomitant formation of the hemiacetal moiety. Use of the t-butyldimethylsilyl) TBS protecting group resulted in low yield, due to its marginal stability to the slightly acidic reaction conditions (pH 2). Tert-butyl diphenyl silyl (TBDPS) protecting group (entry 6, Table 3) gave substantially improved yield.

TABLE 3

| Entry | Substrate | Product | Yield (%) |
|---|---|---|---|
| 1 | 11a | 11b | 75 |
| 2 | 12a | 12b | 78 |
| 3 | 13a | 13b | 97 |
| 4 | 14a | 14b | 33 |
| 5 | 15a | 15b | 86 |

TABLE 3-continued

| Entry | Substrate | Product | Yield (%) |
|---|---|---|---|
| 6 | 16a | 16b | 72 |

Another study explored the C—H oxidation of 5/5 spiroketals (see Table 4, below). No reaction was observed for dibrominated 5/5 spiroketal 17a, presumably due to the combined steric and electronic effect of bromine at C-15. Stoichiometric oxidation of saturated spiroketals 18a and 19a afforded the corresponding tertiary alcohols 18b and 19b, respectively. Our results indicated that the action of Cr[VI] on 20a provided 20b, a potential key intermediate for synthesis of the north unit of cephalostatin analogue, in 66% yield along with 26% of the C-22 spiroketal isomer, as a result of acid catalyzed isomerization (The equilibrium ration between 20b and 20c in $CH_2Cl_2$ in the presence of acid catalyst is 1:1.2). We believe that allylic oxidation of 20a to its corresponding allylic alcohol, followed by hydroxyl directed epoxidaito to epoxy alcohol 20b is the reaction pathway. Evidence in support of C—H oxidation preceding epoxidation is seen in Cr[VI] oxidation of 18a which requires more forcing conditions (−10° C., 1h) to stereospecifically generate lactol epoxide 18b.

TABLE 4

| Entry | Substrate | Product | Yield (%) |
|---|---|---|---|
| 7 | 17a | | NR |
| 8 | 18a | 18b | 80 |
| 9 | 19a | 19b | 91 |

TABLE 4-continued

| Entry | Substrate | Product | Yield (%) |
|---|---|---|---|
| 10 | 20a | 20b / 20c | 66/26 |

Another study focused on the effect of substitution at C-14,15 on the C—H oxidation (Table 5, below). Unlike substrates which possess C-14,15 dihydro (entry 1–6 of Table 3) or 5/5 spiroketal (entry 8–10 of Table 4) 21a and 22a reacted with Cr oxidant to furnish E-ring opening. The formation of 22b can be viewed as sequential allylic oxidation, hydroxyl group directed face epoxidation, followed by E-ring opening. The 5/6 spiroketal 23a with a C-14 OH group was oxidized to afford the corresponding hemiacetal 23c together with 6/6 spiroketal 23b. Sequential oxidation of 23c, followed by acid catalyzed formation of 6/6 spiroketal, seemed to be a reasonable rationale for the formation of 23b. Substitution at C-15 with an electron withdrawing acetate group dramatically changed the site of C—H oxidation. In this instance, the C-16 position, now deactivated by an adjacent acetate group is inert, and oxidation of the C—H bond at C-22 occurs to give hemiacetal 24b, indicated the role of eletronic effects on the regiochemistry of C—H oxidation.

TABLE 5

| Entry | Substrate | Product/yield |
|---|---|---|
| 11 | 21a | 21b — 79% |
| 12 | 22a | 22b — 35% |

TABLE 5-continued
| Entry | Substrate | Product/yield |
|---|---|---|
| | | 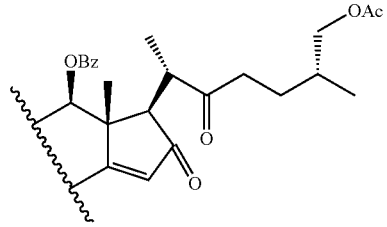 22c 48% |
| 13 | 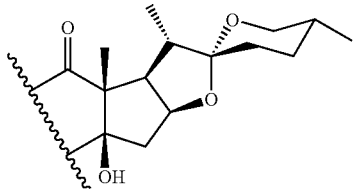 23a | 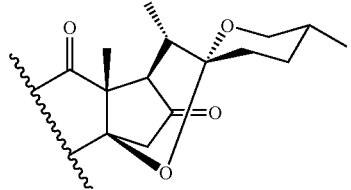 23b 46% |
| | | 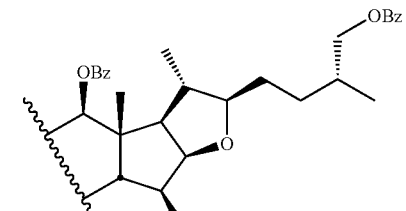 23c 41% |
| 14 | 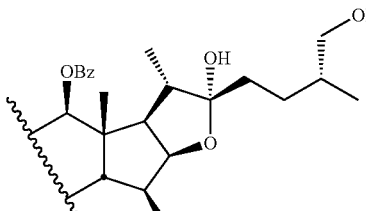 24a | 24b 69% |

The following scheme 3 presented below shows an application of the C—H oxidation of the present invention to the synthesis of the north unit 26 of cephalostatin analogue. Epoxy alcohol 20b, formed by Cr[VI] mediated C—H oxidation, was readily converted into epoxy ketone 25, which is a prospective key itermediate for 26.

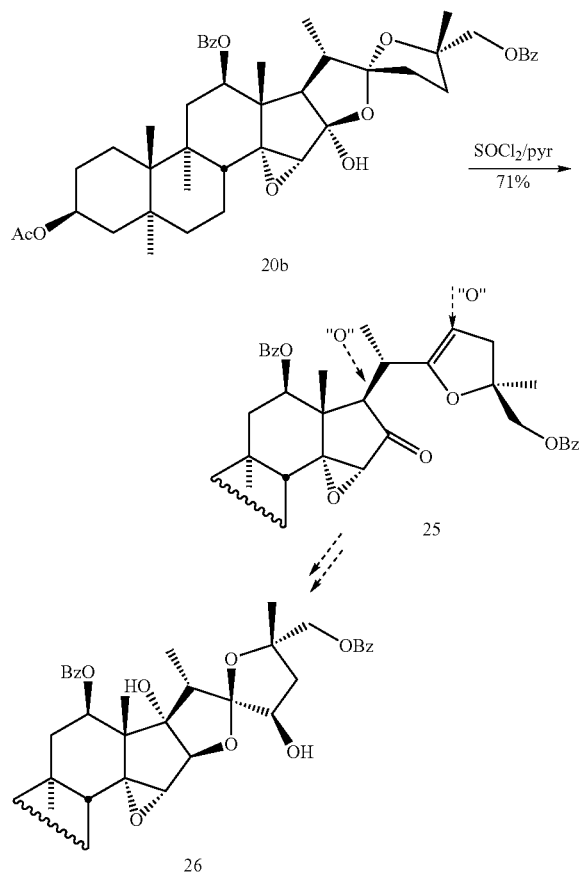

The invention will now be described further by reference to the following specific examples, which are illustrative and in no way limiting.

EXAMPLE 1

General Procedures

All reagents purchased were used as received. Methylene chloride, acetonitrile, and dimethyl formamide were distilled from calcium hydride. Sodium sulfate ($Na_2SO_4$) was anhydrous. All recrystalization, chromatographic, and workup solvents were distilled. Powdered 4A molecular sieves were oven and flame activated prior to use.

Unless otherwise indicated, all reactions were carried out under a positive pressure of argon in anhydrous solvents and the reaction flasks were fitted with rubber septa for the introduction of substrates and reagents via syringe. Progress of reactions was monitored by thin layer chromatography (TLC) in comparison with the starting materials. The two commonly employed visualizing solutions were: (i) p-anisaldehyde solution (1350 mL absolute ethanol, 50 mL concentrated $H_2SO_4$; 37 mL p-anisaldehyde), and (ii) permanganate solution (weight percents of 1% KMnO4 and 2% $Na_2CO_3$ in water).

Analytical samples were obtained from flash silica gel chromatography, using silica gel of 230–400 crystallization of the crude products. $^1$H NMR and $^{13}$C NMR spectra were recorded on General QE-300 (300 MHz). NMR spectra were determined in chloroform-$d_1$ ($CDCl_3$), benzene-$d_6$ ($C_6D_6$) pyridine-$d_5$ ($C_5D_5N$) solution and are reported in parts per million (ppm) from the residual chloroform (7.24 ppm and 77.0 ppm), benzene (7.16 ppm and 128.39 ppm) or pyridine (8.74 ppm and 150.35 ppm) standard respectively. Peak multiplicates in $^1$H-NMR spectra, when reported, are abbreviated as s (singlet), d (doublet), t (triplet), m (multiplet), and/or ap (apparent) and/or br (broad). Mass spectra were run by the Purdue University campus wide mass spectrometry facility.

EXAMPLE 2

Stoichiometric Method

Finely ground anhydrous chromium trioxide (300 mg, 3 mmol) was added to $CH_2Cl2$ (1.5 mL) and $CH_3CN$ (4.5 mL) under a positive pressure of argon and the suspension was stirred vigorously for 30 minutes at ambient temperature. The chromium trioxide suspension was then cool ed to −40° C. and a $CH_2Cl_2$ (1 mL) solution of a compound of formula 5 (562 mg, 1 mmol):

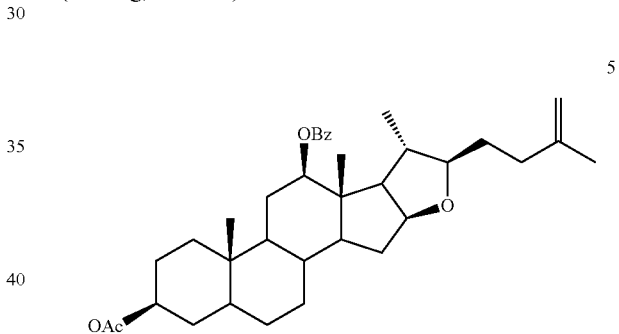

was added in one portion. After stirring 5 min at −40° C., $Bu_4NIO_4$ (1.30 g, 5 mmol) in $CH_3CN$ (3 mL) was added dropwise to the mixture solution of $CrO_3$ and the compound of formula 5 for 10 minutes. The dark orange reaction mixture was quenched by addition of saturated aqueous $Na_2SO_3$, extracted with EtOAc, washed with water, brine, dried over $Na_2SO_4$, concentrated and purified by silica gel column chromatography to yield a hemiacetal of formula 6 (433 mg, 75%, 89% based upon recovered starting material):

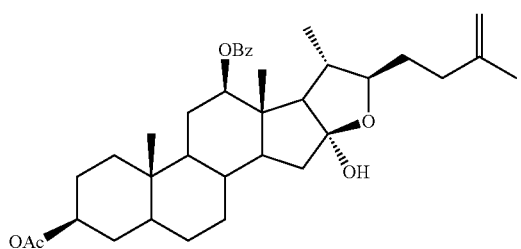

Hemiacetal 6 was determined to have the following properties: $^1$H NMR (300 MHz, CDCl$_3$) δ 7.39–7.89 (5H, m), 4.93 (1H, dd, J=11.1,4.5 Hz), 4.67 (3H, m), 3.81 (1H, m), 2.36 (1H, br), 1.98 (3H, s), 1.70 (3H, s), 0.98 (3H, s), 0.84 (3H, s), 0.77 (3H, d, J=6.7 Hz); $^{13}$C NMR(75 MHz, CDCl$_3$) δ 170.6, 165.6, 145.6, 132.9, 130.6, 129.4, 128.4, 114.7, 109.6, 88.7, 81.7, 73.4, 70.0, 54.2, 52.5, 46.1, 44.4, 39.9, 38.5, 36.5, 35.6, 34.5, 34.0, 33.8, 31.7, 31.4, 28.3, 27.2, 26.7, 22.6, 21.4, 18.2, 12.1, 10.9; MS (ESI) 601 (M+Na); HRMS (ESI) calculated for C$_{36}$H$_{50}$O$_6$ (M+Na) 601.3505, found 601.3510.

EXAMPLE 3

Catalytic Method

To a freshly prepared CH$_2$Cl$_2$ solution of chromyl diacetate (O$_2$Cr(OAc)$_2$, 1 mL, 1 M) was added dropwise a CH$_3$CN solution of H$_5$IO$_6$ (0.33 M, 3 mL) at –40° C. for 10 minutes to give a deep orange solution which is stable at –40° C. for several hours. In a different flask, a CH$_2$Cl$_2$ (0.4 mL) solution of ethyl benzene (212 mg, 2 mmol) and acetic anhydride (0.38 mL, 4 mmol, 2 eq) was cooled to –40° C. The earlier prepared chromium oxidant solution (0.4 mL, 0.25 M. 5 mol %) was added in one portion to the solution of starting material, followed; by the addition of a CH$_3$CN solution of H$_5$IO$_6$ (0.33 M, 18.2 mL, 3 eq) at –40° C. over a period of 30 minutes. The resulting orange colored reaction mixture was gradually warmed up to 0° C. for a period of 1.5 h, quenched by addition of saturated aqueous Na$_2$SO$_4$, extracted with EtOAc, washed with water, brine, dried over Na$_2$SO$_4$, concentrated and purified by silica gel column chromatography to give acetophenone (231 mg, 96%).

EXAMPLE 4

NMR and Mass Spectrometry Characterization of Reactants and Products

Proton NMR, carbon NMR, mass spectrometry and high resolution mass spectrometry characterizations of the aforementioned compounds of formulae 1, 3α, 3β, 4α, 4β, 6, 8, and 10 were determined to be as follows.

Δ$^{14}$-Spiroketal 1: $^1$H NMR (300 MHz, CDCl$_3$) δ7.39–8.13 (5H, m), 5.30 (1H, s), 4.86 (1H, dd, J=8.1.1.5 Hz), 4.63 (2H, m), 4.34 (1H, d, J=11.1 Hz), 4.18 (1H, d, J=11.1 Hz), 2.40 (1H, m), 2.25 (1H, m), 1.99 (3H, s), 1.21 (3H, s), 1.19 (3H, s), 0.88 (3H, d, J=10.5 Hz), 0.86 (3H, s); $^{13}$C NMR (75 MHz, CDCl$_3$) δ 170.5, 166.4, 165.8, 156.5, 132.9, 132.8, 130.6, 130.4, 129.8, 129.5, 128.3, 128.3, 120.2, 117.6, 84.4, 82.4, 81.5, 73.2, 70.2, 56.1, 52.0, 51.6, 44.2, 41.0, 36.5, 35.9, 34.0, 33.8, 32.8, 32.3, 29.4, 28.1, 27.2, 26.6, 24.0, 21.4, 15.3, 14.1, 14.0, 11.9; MS (ESI) 719 (M+Na); HRMS (ESI) calculated for C$_{43}$H$_{52}$O$_8$ (M+Na) 719.3560, found 719.3563.

Epoxy alcohol 3α: $^1$H NMR (300 MHz, CDCl$_3$) δ 7.34–8.13 (10H, m), 4.65 (1H, m), 4.37 (2H, m), 4.10 (1H, s), 3.38 (1H, s), 2.37 (1H, m), 1.98 (3H, s), 1.22 (3H, s), 1.12 (3H, s), 0.86(3H, s), 0.84 (3H, d); $^{13}$C NMR (75 MHz, CDCl$_3$) δ 170.4, 166,4, 165.3, 132.9, 132.8, 130.4, 129.9, 129.5, 129.3, 128.3, 128.2, 121.2, 113.2, 83.8, 78.8, 73.2, 72.4, 69.7, 62.0, 59.8, 48.2, 46.4, 43.6, 39.2, 36.2, 35.6, 35.0, 33.7, 32.2, 31.2, 27.4, 27.2, 26.4, 24.9, 23.6, 21.3, 16.0, 14.2, 11.8; MS (ESI) 751 (M+Na); HRMS (ESI) calculated for C$_{43}$H$_{52}$O$_{10}$ (M+H) 729.3639, found 729.3638; single crystal X-ray.

Epoxy alcohol 3β. $^1$H NMR (300 MHz, CDCl$_3$) δ 7.37–8.13 (10H, m), 5.06 (1H, dd, J=11.5, 4.4 Hz), 4.64 (m, 1H), 4.59 (1H, d, J=11.5 Hz), 4.13 (1H, d, J=11.3 Hz), 3.98 (1H, s), 3.40 (1H, s), 2.20 (2H, m), 1.99 (3H, s), 1.59 (3H, s), 1.24 (3H, s), 1.16 (3H, s), 0.84 (3H, s); $^{13}$C NMR (75 MHz, CDCl$_3$) δ; 170.5, 166.7, 165.7, 132.9, 132.8, 130.5, 130.0, 129.9, 129.4, 128.4, 128.3, 118.5, 110.0, 83.2, 75.4, 73.2, 70.4, 62.3, 61.4, 52.4, 47.4, 46.3, 44.0, 43.0, 36.3, 35.7, 33.7, 32.5, 32.4, 32.2, 27.5, 27.2, 26.3, 25.8, 25.0, 23.6, 21.4, 20.1, 13.7, 13.5, 11.9, 10.6; MS (ESI) 751 (M+Na) HRMS (ESI) calculated for C$_{43}$H$_{52}$O$_{10}$ (M+H) 729.3639, found 729.3643.

Epoxy spiroketal 4α. $^1$H NMR (300 MHz, CDCl$_3$) δ 7.37–8.03 (10H, m), 4.63 (3H, m), 4.12 (1H, d, J=11.1 Hz) 3.96 (1H, d, J=11.2 Hz), 3.47 (1H, s), 2.20 (2H, m), 1.98 3H, s), 1.38 (3H, s), 1.27 (3H, s), 0.84 (6H); $^{13}$C NMR (75 MHz, CDCl$_3$) δ; 170.6, 166.3, 166.0, 133.1, 132.9 130.3, 130.1, 129.8, 129.5, 129.4, 128.4, 128.3, 119.2, 82.3, 79.6, 78.2, 75.7, 73.1, 69.7, 60.4, 53.8, 48.0, 46.8, 44.2, 41.7, 36.4, 35.7, 33.7, 33.6, 33.2, 32.4, 27.5, 27.1, 26.5, 26.1, 25.8, 21.4, 14.2, 12.0, 10.4; MS (ESI) 735 (M+Na); HRMS (ESI) calculated for C$_{43}$H$_{52}$O$_9$ (M+H) 713.3690, found 713.3685.

Epoxy spiroketal 4β. $^1$H NMR (300 MHz, CDCl$_3$) δ 7.42–8.10 (10H, m), 4.63 (1H, m), 4.57 (1H, dd, J=11.4, 4.3 Hz), 4.51 (1H, dd, J=8.4, 1.5 Hz), 4.29 (1H, d, J=11.0 Hz), 4.16 (1H, d, J=11.0 Hz), 3.38 (1H, s), 2.20 (2H, m), 1.98 (3H, s), 1.28 (3H, s), 1.15, (3H, s), 0.88 (3H, d, J=5.4 Hz), 0.83 (3H, s); $^{13}$C NMR (75 MHz, CDCl$_3$) δ; 170.6, 166.4, 165.9, 133.0, 132.8, 130.4, 130.3, 129.7, 129.5, 128.4, 128.3, 119.2, 82.3, 79.5, 77.4, 77.0, 76.6, 75.8, 73.1, 70.2, 60.4, 53.8, 47.9, 46.8, 44.2, 41.7, 36.4, 35.7, 33.7, 33.6, 32.8, 32.7, 32.6, 27.5, 27.1, 26.5, 26.1, 25.8, 21.4, 14.2, 12.0, 10.4; MS (ESI) 735 (M+Na); HRMS (ESI) calculated for C$_{43}$H$_{52}$O$_9$ (M+H) 713.3690, found 713.3687.

Hemiacetal 6. $^1$H NMR (300 MHz, CDCl$_3$) δ 7.38–8.00 (5H, m), 4.90 (1H, dd, J=11.1, 4.5Hz) 4.67 (3H, m), 3.82 (1H, m), 2.37 (1H, br), 1.98 (3H, s), 1.70 (3H, s), 0.98 (3H, s), 0.83 (3H, s), 0.77 (3H, d, J=7.7 Hz), 0.83 (3H, s); $^{13}$C NMR (75 MHz, CDCl$_3$) δ; 170.6, 166.6, 145.6, 132.9, 130.6, 129.4, 128.4, 114.7, 109.6, 88.7, 81.7, 73.4, 70.0, 54.2, 52.5, 46.0, 44.4, 39.9, 38.5, 36.5, 35.6, 34.5, 34.0, 33.8, 31.7, 31.4, 28.3, 27.3, 26.7, 22.6, 21.4, 18.1, 12.1, 10.9; MS (ESI) 601 (M+Na); HRMS (ESI) calculated for C$_{36}$H$_{50}$O$_6$ (M+Na) 601.3505, found 601.3510.

α,β-Unsaturated ketone 8. $^1$H NMR (300 MHz, CDCl$_3$) δ 5.38 (1H, m), 4.60 (3H, m), 2.98 (1H, d, J=7.8 Hz), 2.16–2.52 (6H, m), 2.11 (3H, s), 1.96 (3H, s), 1.66 (3H, s), 1.33 (3H, s), 0.87 (3H, s); $^{13}$C NMR (75 MHz, CDCl$_3$) δ; 212.4, 204.3, 172.8, 170.7, 144.0, 110.6, 73.2, 73.0, 58.9, 57.0, 56.4, 54.1, 44.7, 37.4, 36.5, 36.4, 34.7, 34.0, 33.9, 32.8, 32.6, 31.3, 30.9, 28.3, 27.4, 22.8, 21.6, 14.0, 12.1; MS (ESI) 467 (M+H)); HRMS (ESI) calculated for C$_{29}$H$_{40}$O$_5$ (M+H) 469.2954, found 469.2970.

α,β-Unsatuarated ketone 10. $^1$H NMR (300 MHz, CDCl$_3$) δ 5.38 (1H, m), 4.60 (1H, m), 3.12 (2H, m), 3.00 (1H, d, J=7.8 Hz), 2.40 (2H, m), 2.18 (2H, m), 2.11 (3H, s), 1.94 (3H, s), 1.31 (3H, s), 0.90 (3H, d, J=6.1 Hz), 0.86 (3H, s); $^{13}$C NMR (75 MHz, CDCl$_3$) δ; 212 172.8, 170.8, 73.3, 73.0, 58.8, 57.2, 56.3, 54.0, 44.7, 37.6, 36.5, 36.4, 34.0, 34.0, 33.9, 31.5, 31.3, 31.1, 28.3, 27.4, 21.6, 20.4, 16.7, 14.0, 12.1; MS (ESI) 615 (M+H$_2$O); HRMS (ESI) calculated for C$_{29}$H$_{41}$IO$_5$ (M+H) 597.2077, found 597.2073.

EXAMPLE 5

Experimental for Compounds 11b–26c

General Procedures

All reagents, including $CrO_3$ and $Bu_4NIO_4$, purchased were used as received. Methylene chloride, acetonitrile, and were distilled from calcium hydride. Sodium sulfate ($Na_2SO_4$) was anhydrous. All recrystalization, chromatographic, and workup solvents were distilled.

Unless otherwise indicated, all reactions were carried out under in a positive pressure of argon in anhydrous solvents and the reaction flasks were fitted with rubber septa for the introduction of substrates and reagents via syringe. Progress of reactions was monitored by thin layer chromatography (TLC) in comparison with the starting materials. The two commonly employed TLC visualizing solutions were: (i) p-anisaldehyde solution (1350 mL absolute ethanol, 50 mL concentrated $H_2SO_4$, 37 mL p-anisaldehyde), and (ii) permanganate solution (weight percents of 1% $KMnO_4$ and 2% $Na_2CO_3$ in water).

Analytical samples were obtained from flash silica gel chromatography, using silica gel of 230–400 crystalization of the crude products. $^1H$ NMR and $^{13}C$ NMR spectra were recorded on General Electric QE-300 (300 MHz). NMR spectra were determined in chloroformd-$d_1$ ($CDCl_3$), benzene-$d_6$ ($C_6D_6$) or pyridine-$d_5$ ($C_5D_5N$) solution and are reported in parts per million (ppm) from the residual chloroform (7.24 ppm and 77.0 ppm), benzene (7.16 ppm and 128.39 ppm) or pyridine (8.74 ppm and 150.35 ppm) standard respectively. Peak multiplicates in $^1H$-NMR spectra, when reported, are abbreviated as s (singlet), d (doublet), t (triplet), m (multiplet), and/or ap (apparent) and/or br (broad). Mass spectra were run by the Purdue University campus wide mass spectrometry facility.

Representative Experimental Procedure for Compounds 11b–26c (All compounds are prepared using this procedure by strict analogy:

Stoichiometric Method: $CrO_3/Bu_4NIO_4$. Anhydrous chromium trioxide (300 mg, 3 mmol) was finely ground in $CH_2CL_2$ (1.5 mL) and $CH_3CN$ (4.5 mL) under a positive pressure of argon and the suspension was stirred vigorously for 10 min at ambient temperature. The chromium trioxide suspension was then cooled to −40° C. and a $CH_2Cl_2$ (1 mL) solution of 12a (698 mg, 1 mmol) was added in one portion. After stirring 5 min at −40° C., $Bu_4NIO_4$ (1.30 g, 5 mmol) in $CH_3CN$ (3 mL) was added dropwise to the mixture solution of $CrO_3$ and 12a for 10 min. The dark orange reaction mixture was quenched by addition of saturated aqueous $Na_2SO_3$, extracted with EtOAc, washed with water, brine, dried over $Na_2SO_4$, concentrated and purified by silica gel column chromatography to give hemiacetal 12b (649 mg, 91%)

11b. $^1H$ NMR (300 MHz, $CDCl_3$) δ 7.39–7.89 (5H, m), 4.93 (1H, dd, J=11.1, 4.5 Hz), 4.67 (3H, m), 3.81 (1H, m), 2.36 (1H, br), 1.98 (3H, s), 1.70 (3H, s), 0.98 (3H, s), 0.84 (3H, s), 0.77 (3H, d, J=6.7 Hz); $^{13}C$ NMR (75 MHz, $CDCl_3$) δ 170.6, 165.6, 145.6, 132.9, 130.6, 129.4, 128.4, 114.7, 109.6, 88.7, 81.7, 73.4, 70.0, 54.2, 52.5, 46.1, 44.4, 39.9, 38.5, 36.5, 35.6, 34.5, 34.0, 33.8, 31.7, 31.4, 28.3, 27.2, 26.7, 22.6, 21.4, 18.2, 12.1, 10.9; MS (ESI) 601 (M+Na); HRMS (ESI) calculated for $C_{36}H_{50}O_6$ (M+Na) 601.3505, found 601.3510

12b. $^1H$ NMR (300 MHz, $CDCl_3$) δ 5.26 (1H, m), 4.76–4.60 (4H, m), 3.94 (1H, dd, J=8.5, 4.4 Hz), 2.31 (1H, br), 2.03 (6H, s), 1.98 (3H, s), 1.03 (3H, d, J=6.8 Hz), 0.87 (6H, br), 0.81 (3H, s); $^{13}C$ NMR (75 MHz, $CDCl_3$) δ 170.4, 170.1, 170.0, 141.0, 114.6, 113.1, 88.9, 80.9, 73.1, 71.5, 69.9, 53.8, 52.2, 45.6, 44.2, 39.5, 39.2, 36.2, 35.3, 34.4, 33.6, 33.5, 31.3, 31.2, 28.0, 27.0, 26.3, 25.0, 22.3, 22.1, 21.1, 20.7, 19.1, 13.9, 11.8, 10.3; MS (ESI) 597 (M+Na); HRMS (ESI) calculated for $C_{33}H_{50}O_8$ (M+Na), found 14b. $^1H$ NMR (300 MHz, $CDCl_3$) δ 7.39–8.05 (5H, m), 4.86 (1H, dd, J=11.1, 4.6 Hz), 4.67 (1H, m), 3.82 (1H, m), 2.42 (1H, m), 1.16 (3H, d, J=8.0 Hz), 0.97 (3H, s), 0.83 (3H, s), 0.75 (3H, d, J=6.5 Hz); $^{13}C$ NMR (75 MHz, $CDCl_3$) δ 181.1, 170.6, 165.6, 132.9, 130.6, 129.4, 128.4, 114.9, 88.8, 81.6, 73.4, 69.8, 54.2, 52.5, 46.1, 44.5, 39.8, 39.3, 38.5, 36.5, 35.6, 34.0, 33.8, 31.4, 31.0, 30.6, 28.3, 27.3, 26.7, 21.4, 18.0, 17.0, 12.1, 10.9; MS (ESI) 633 (M+Na); HRMS (ESI) calculated for $C_{36}H_{50}O_8$ (M+Na) 633.3403, found 633.3405

15b. $^1H$ NMR (300 MHz, $CDCl_3$) δ 7.35–8.00 (5H, m), 4.86 (1H, dd, J=11.1, 4.5 Hz), 4.62 (1H, m), 3.84 (2H, m), 3.76 (1H, m), 2.72 (1H, s), 1.99 (3H, s), 1.96 (3H, s), 0.96 (3H, s), 0.88 (3H, d, J=6.2 Hz), 0.82 (3H, s), 0.74 (3H, d, J=6.7 Hz); $^{13}C$ NMR (75 MHz, $CDCl_3$) δ 171.1, 170.5, 165.6, 132.8, 130.5, 129.3, 128.3, 114.5, 88.9, 81.6, 73.3, 69.9, 69.2, 54.1, 52.4, 44.9, 44.4, 39.9, 38.5, 36.4, 35.5, 33.9, 33.7, 32.5, 31.4, 30.9, 30.2, 28.2, 27.2, 26.6, 21.3, 20.8, 18.0, 16.7, 12.0, 10.9; MS (ESI) 661 (M+Na); HRMS (ESI) calculated for $C_{38}H_{54}O_8$ (M+Na) 661.3716, found 661.3717

16b $^1H$ NMR (300 MHz, $CDCl_3$) δ 7.35–8.02 (5H, m), 4.86 (1H, dd, J=11.2, 4.6 Hz), 4.64 (1H, m), 3.79 (1H, m), 3.38 (2H, m), 2.30 (1H, s), 1.99 (3H, s), 1.96 (3H, s), 0.96 (3H, s), 0.88 (3H, d, J=6.2 Hz), 0.82 (3H, s), 0.74 (3H, d, J=6.7 Hz); $^{13}C$ NMR (75 MHz, $CDCl_3$) δ 171.1, 170.5, 165.6, 132.8, 130.5, 129.3, 128.3, 114.5, 88.9, 81.6, 73.3, 69.9, 69.2, 54.1, 52.4, 44.9, 44.4, 39.9, 38.5, 36.4, 35.5, 33.9, 33.7, 32.5, 31.4, 30.9, 30.2, 28.2, 27.2, 26.6, 21.3, 20.8, 18.0, 16.7, 12.0, 10.9; MS (ESI) 733 (M+Na); HRMS (ESI) calculated for $C_{38}H_{54}O_8$ (M+Na) 733.3644, found 733.3656

17b $^1H$ NMR (300 MHz, $CDCl_3$) δ 7.35–8.02 (5H, m), 4.87 (1H, dd, J=11.2, 4.6 Hz), 4.65 (1H, m), 3.78 (1H, m), 3.19 (2H, m), 2.36 (1H, s), 1.98 (3H, s), 0.99 (3H, s), 0.95 (3H, d, J=6.1 Hz), 0.83 (3H, s), 0.78 (3H, d, J=6.7 Hz); $^{13}C$ NMR (75 MHz, $CDCl_3$) δ170.6, 165.6, 132.9, 130.6, 129.4, 128.4, 114.8, 88.9, 81.6, 73.4, 70.0, 54.2, 52.5, 46.1, 44.5, 40.0, 38.6, 36.5, 35.6, 34.5, 34.0, 33.8, 33.4, 31.4, 31.0, 28.3, 27.3, 26.7,21.4, 20.6, 18.4, 17.7, 12.1, 10.9, 10.6; MS (ESI) (M+Na) 729; HRMS (ESI) calculated for $C_{36}H_{51}O_8I$(M+Na)729.2628, found 729.2632

20b. $^1H$ NMR (300 MHz, $CDCl_3$) δ 7.35–8.02 (10H, m), 5.03 (1H, dd, J=11.4, 4.1 Hz), 4.12 (1H, d, J=11.3 Hz), 3.96 (1H, d, J=11.3 Hz),3.42 (1H, s), 3.03 (1H, s), 2.16 (1H, m), 1.98 (3H, s), 1.43 (3H, s), 1.23 (3H, s), 0.82 (3H, s), 0.80 (3H, d, J=6.3 Hz); $^{13}C$ NMR (75 MHz, $CDCl_3$) δ 170.6, 166.3, 166.0, 133.1,132.9, 130.2, 130.0, 129.5, 129.4, 128.5, 128.4, 118.7, 110.1, 82.9, 77.5, 75.4, 73.2, 69.6, 62.6, 61.1, 47.5, 46.4, 44.0, 43.0, 36.3, 35.7, 33.6, 33.2, 33.1, 32.4, 27.4, 27.2, 26.3, 26.0, 25.9, 21.4, 13.8, 12.0, 10.4; MS (ESI) (M+Na) 751; HRMS (ESI) calculated for $C_{43}H_{52}O_{10}$ (M+Na) 729.3636, found 729.3638

21b. $^1H$ NMR (300 MHz, $CDCl_3$) δ 7.40–8.13 (1OH, m), 4.94(11H, dd, J=11.0, 4.6 Hz), 4.64 (m, 1H), 4.37 (2H, m), 4.04 (1H, s), 1.99 (3H, s), 1.17 (3H, s), 0.98 (3H, s), 0.84 (3H, s), 0.76 (3H, d, J=6.8 Hz); $^{13}C$ NMR (75 MHz, $CDCl_3$) δ;170.6, 166.3, 165.5, 132.9, 132.8, 130.6, 129.9, 129.8, 129.4, 128.3, 128.2, 121.5, 115.0, 83.6, 81.6, 73.3, 70.0, 69.4, 53.5, 52.4, 46.3, 44.4, 39.5, 37.8, 36.4, 35.5, 33.7, 32.8, 32.6, 31.4, 28.2, 27.2, 26.8, 23.5, 21.3, 13.7, 12.0, 10.7; MS (ESI) (M+Na) 737 HRMS (ESI) calculated for $C_{43}H_{54}O_9$ (M+H) 737.3666, found 737.3656

22b. $^1$H NMR (300 MHz, CDCl$_3$) δ7.40–8.13 (5H, m), 4.86 (1H, d, J=8.0 Hz), 4.64 (2H, m), 4.22 (1H, s), 3.90 (2H, m), 3.56 (1H, s), 2.98–2.54 (2H, m), 2.02 (3H, s), 1.99 (3H, s), 1.37 (3H, s), 0.94 (3H, d, J=6.9 Hz), 0.87 (3H, s), 0.76 (3H, d, J=6.3 Hz); $^{13}$C NMR (75 MHz, CDCl$_3$) δ; 208.5, 170.6, 165.9, 133.2, 130.0, 129.5, 128.5, 107.7, 83.1, 75.6, 73.1, 68.3, 60.2, 53.0, 48.0, 46.9, 44.2, 42.5, 38.6, 36.4, 35.7, 33.6, 32.3, 29.0, 27.4, 27.2, 26.8, 25.8, 21.4, 20.9, 16.8, 13.8, 12.0, 10.5; MS (ESI) (M+Na) 703 HRMS (ESI) calculated for C$_{38}$H$_{50}$O$_9$ (M+H) 737.3666

25b. $^1$H NMR (300 MHz, CDCl$_3$) δ 7.36–8.02 (10 H, m), 5.43 (1H, dd, J=9.9, 6.9 Hz), 4.56–4.77 (m, 3H), 4.16 (2H, m), 2.44 (1H, m), 1.99 (3H, s), 1.98 (3H, s), 1.20 (3H, s), 0.99 (6H), 0.82 (3H, s); $^{13}$C NMR (75 MHz, CDCl$_3$) δ; 170.4, 170.2, 166.5, 166.0, 132.9, 132.8, 130.5, 130.0, 129.9, 129.4, 128.4, 128.3, 86.6, 77.8, 76.5, 74.1, 73.2, 69.5, 57.9, 51.0, 45.7, 43.8, 43.7, 41.0, 36.5, 35.6, 33.7, 32.7, 32.3, 30.8, 30.3, 29.8, 28.5, 27.0, 26.1, 21.2, 20.7, 16.9 16.6, 15.0, 12.1; MS (ESI) 781(M+Na)

26b. $^1$H NMR (300 MHz, CDCl$_3$) δ 4.64 (1H, m), 3.21–3.39 (2H, m), 2.00 (3H, s), 1.27 (3H, s), 1.00 (3H, d, J=6.0 Hz), 0.95 (3H, s), 0.76 (3H, d, J=5.8 Hz); see X-ray 26c. $^1$H NMR (300 MHz, CDCl$_3$) δ 4.62 (1H, m), 3.56 (2H, m), 3.42 (1H, s), 3.21 (1H, d, J=7.5 Hz), 1.99 (3H, s), 1.18 (3H, s), 0.99 (3H, d, J=7.0 Hz), 0.87 (3H, s), 0.79 (3H, d, J=6.2Hz); $^{13}$C NMR (75 MHz, CDCl$_3$) δ; 211.5, 169.5, 113.2, 106.4, 84.8, 72.9, 66.7, 61.8, 58.0, 46.2, 45.6, 39.0, 36.9, 36.7, 36.2, 33.7, 31.6, 29.7, 28.2, 27.8, 26.9, 26.5, 21.1, 16.5, 14.5, 14.2, 11.7; MS (ESI) (M+Na) 527 HRMS (ESI) calculated for C$_{29}$H$_{44}$O$_7$ (M+H) 505.3655, found 505.3652

What is claimed is:

1. A method of oxidizing a hydrocarbon according to the chemical structure:

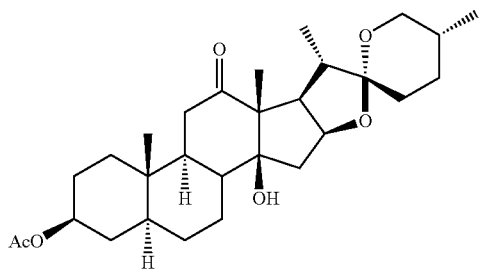

comprising reacting the hydrocarbon in an anhydrous solvent with a chromium [VI] oxidant and a co-oxidant at a reaction temperature of between about –50° C. to about 0° C., thereby catalytically and chemospecifically oxidizing the hydrocarbon: (i) substantially stereospecifically at a tertiary carbon to form a hemiacetal according to the structure:

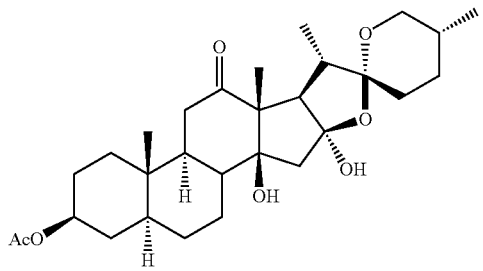

wherein the chromium [VI] oxidant is selected from the group consisting of CrO3, chromoyl diacetate, chromoyl chloride, chromoyl bistrifluoroacetate, chromoyl bistriflate, and chromoyl bis t-butylester, the co-oxidant is selected from the group consisting of periodic acid, tetrabutylammonium periodate, hydrogen peroxide, t-butyl hydroperoxide, diacyl peroxides, TMSOOTMS, peroxydisulfate and persulfate, and the solvent is selected from the group consisting of acetic acid, acetonitrile, methylene chloride and mixtures, thereof.

2. The method of claim 1, wherein the chromium [VI] oxidant is chromoyl diacetate, the co-oxidant is periodic acid or tetrabutylammonium periodate, the solvent is a mixture of acetonitrile and methylene chloride, the reaction time is from about thirty minutes to about three hours, and the reaction takes place under a positive pressure of inert gas.

3. The method of claim 1, wherein a mixture solution of the hydrocarbon, chromium [VI] oxidant and an aqueous solvent is formed and a mixture of co-oxidant and aqueous solvent is added to the mixture solution.

4. The method of claim 3, wherein the mixture solution of hydrocarbon, chromium [VI] oxidant and anhydrous solvent comprises CrO$_3$, methylene chloride and acetonitrile and the mixture of co-oxidant and an anhydrous solvent comprises periodic acid and acetonitrile.

5. The method of claim 3, wherein the mixture solution of hydrocarbon, chromium [VI] oxidant and anhydrous solvent comprises chromoyl diacetate, methylene chloride and acetonitrile and the mixture of co-oxidant and anhydrous solvent comprises tetrabutylammonium periodate and acetonitrile.

6. The method of claim 4 or 5, wherein the reaction temperature is approximately –50° C. to approximately –20° C.

7. The method of claim 6, wherein the reaction temperature is approximately –40° C.

8. A method of oxidizing a hydrocarbon according to the structure:

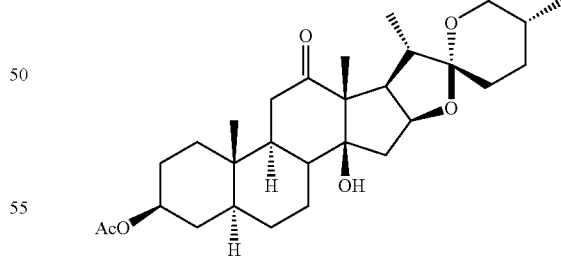

comprising reacting the hydrocarbon in an anhydrous solvent with a CrO$_3$ or chromoyl diacetate oxidant and a periodic acid or tetrabutylammonium periodate co-oxidant at a reaction temperature of between about –60° C. to about –20° C., thereby catalytically and chemospecifically oxidizing the hydrocarbon substantially stereospecifically at a tertiary C—H bond to form a hemiacetal according to the structure:

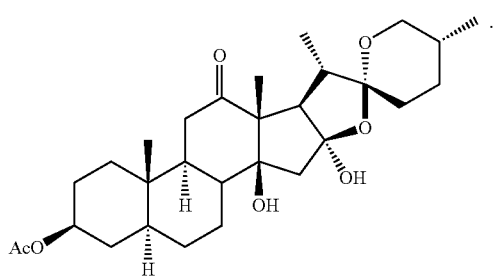

9. The method according to claim 8 wherein said anhydrous solvent is selected from the group consisting of methylene chloride, acetonitrile and mixtures thereof.

10. The method according to claim 8 wherein said solvent is a mixture of methylene chloride and acetonitrile.

11. The method according to claim 8 wherein said oxidant is $CrO_3$ and said co-oxidant is tetrabutylammonium periodate.

* * * * *